(12) United States Patent
Kaminski

(10) Patent No.: US 8,578,941 B2
(45) Date of Patent: Nov. 12, 2013

(54) SLIPPER-LIKE DEVICE TO PREVENT OR HELP HEAL PRESSURE ULCERS OF THE FOOT

(76) Inventor: Mitchell V. Kaminski, Niles, IL (US)

( * ) Notice: Subject to any disclaimer, the term of this patent is extended or adjusted under 35 U.S.C. 154(b) by 244 days.

(21) Appl. No.: 12/986,654

(22) Filed: Jan. 7, 2011

(65) Prior Publication Data

US 2011/0168191 A1 Jul. 14, 2011

Related U.S. Application Data

(60) Provisional application No. 61/293,510, filed on Jan. 8, 2010.

(51) Int. Cl.
*A61F 5/37* (2006.01)
(52) U.S. Cl.
USPC .......................................................... 128/882
(58) Field of Classification Search
USPC ......... 128/869, 878, 879, 881, 885, 892, 893, 128/894; 602/5, 18, 23, 27, 60, 62, 63, 65, 602/28, 29; 119/851; 607/111
See application file for complete search history.

(56) References Cited

U.S. PATENT DOCUMENTS

| | | | | |
|---|---|---|---|---|
| 3,693,619 A | * | 9/1972 | Williams | 128/892 |
| 4,243,028 A | * | 1/1981 | Puyana | 602/62 |
| 5,545,129 A | * | 8/1996 | Snook | 602/66 |
| 5,618,263 A | * | 4/1997 | Alivizatos | 602/6 |
| 6,585,673 B1 | * | 7/2003 | Bass | 602/60 |
| 6,794,554 B2 | * | 9/2004 | Sessions et al. | 602/46 |
| 8,122,550 B2 | * | 2/2012 | Johnson | 12/146 M |
| 2006/0069334 A1 | * | 3/2006 | Moskowitz | 602/5 |
| 2006/0276737 A1 | * | 12/2006 | Rose | 602/30 |
| 2008/0256706 A1 | * | 10/2008 | Larsen | 5/425 |

OTHER PUBLICATIONS http://www. nextag.com/heel-protector/compare-html. NexTag Comparison Shopping. copyright 1999-2009, NexTag, Inc., 3 pages.
http://www.posey.com/Posey/Woundcare-Prevention/Footcare/P..., Pro-HeeLx-Woundcare Prevention-Footcare-Posey Co., copyright 2009 Posey Company, Arcadia, CA, 2 pages.
Webpage for Heelift Standard Suspension Boot, Evanston, Illinois. copyright 2008 DM Systems, Inc., 2 pages.
Webpage for EHOB Clinical Catalog, EHOB, Incorporated, Indianapolis, Indiana. copyright 2006-2009 EHOB, Inc., 2 pages.

* cited by examiner

*Primary Examiner* — Patricia Bianco
*Assistant Examiner* — Raymond E Harris
(74) *Attorney, Agent, or Firm* — Vedder Price P.C.

(57) ABSTRACT

A foot garment device to prevent or help prevent or heal pressure ulcers of the foot includes a bumper for positioning around and below an ankle of an individual, and one or more upper adjustable flaps and one or more lower adjustable flaps for removably securing the foot garment to a foot of the individual, wherein the bumper includes a hollow sleeve for receiving padding therein. Also described is a method for securing such a foot garment device to the foot of an the individual.

20 Claims, 26 Drawing Sheets

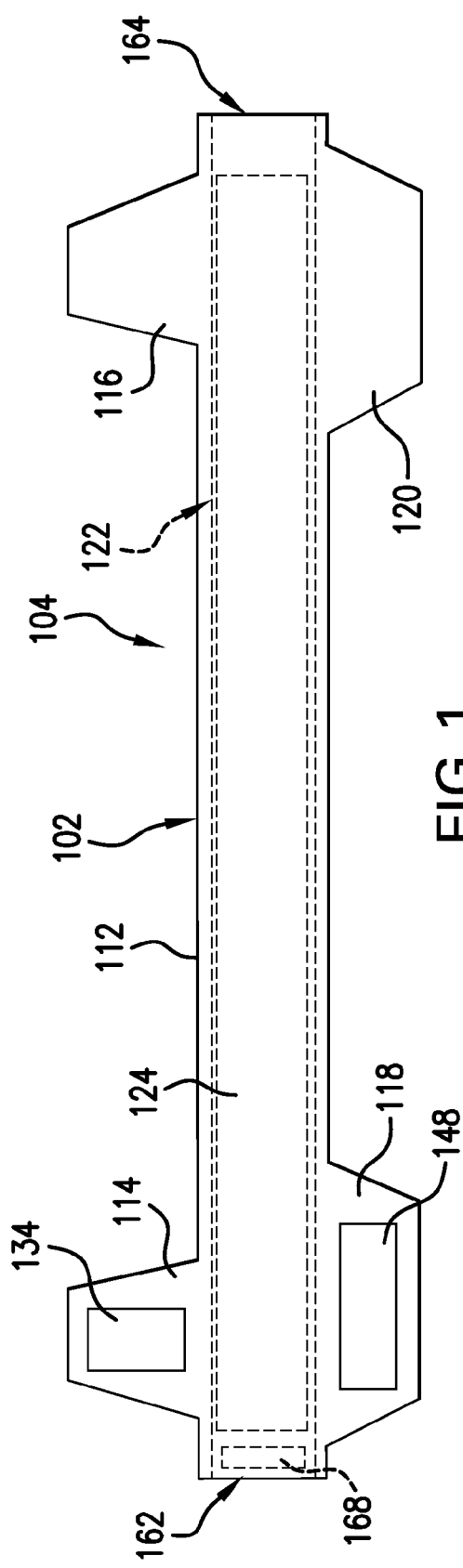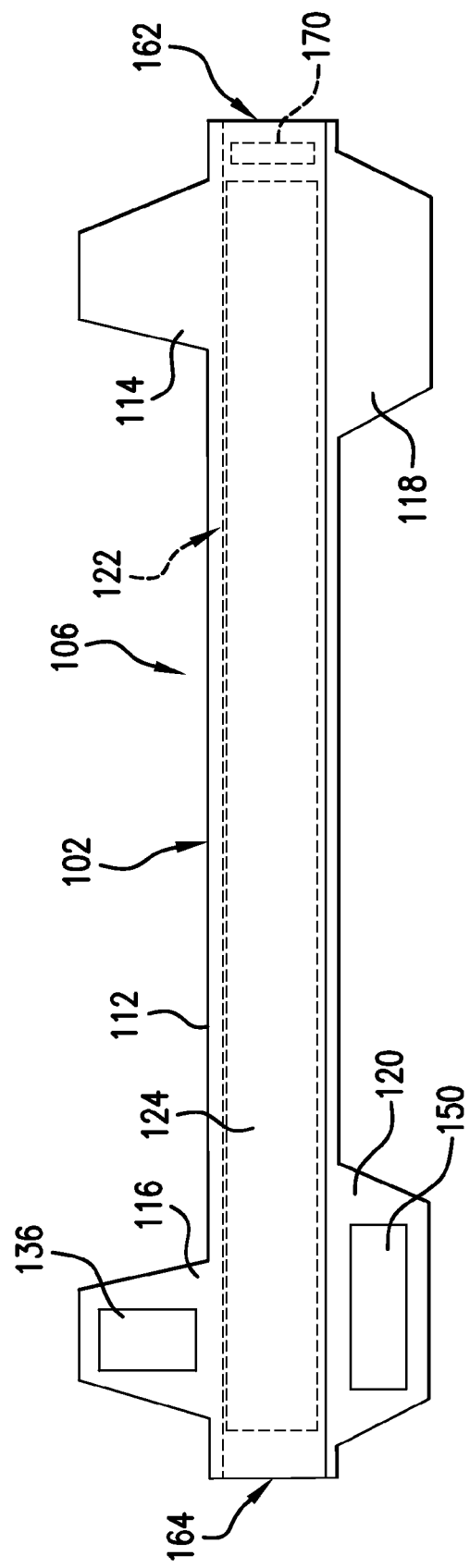

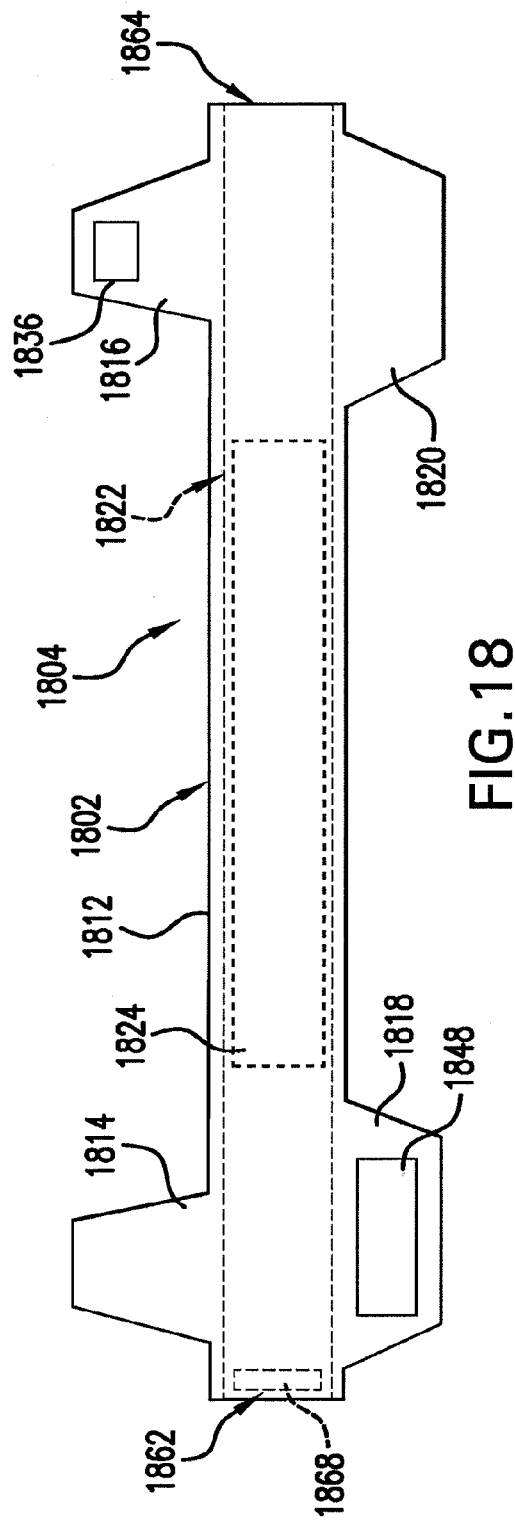
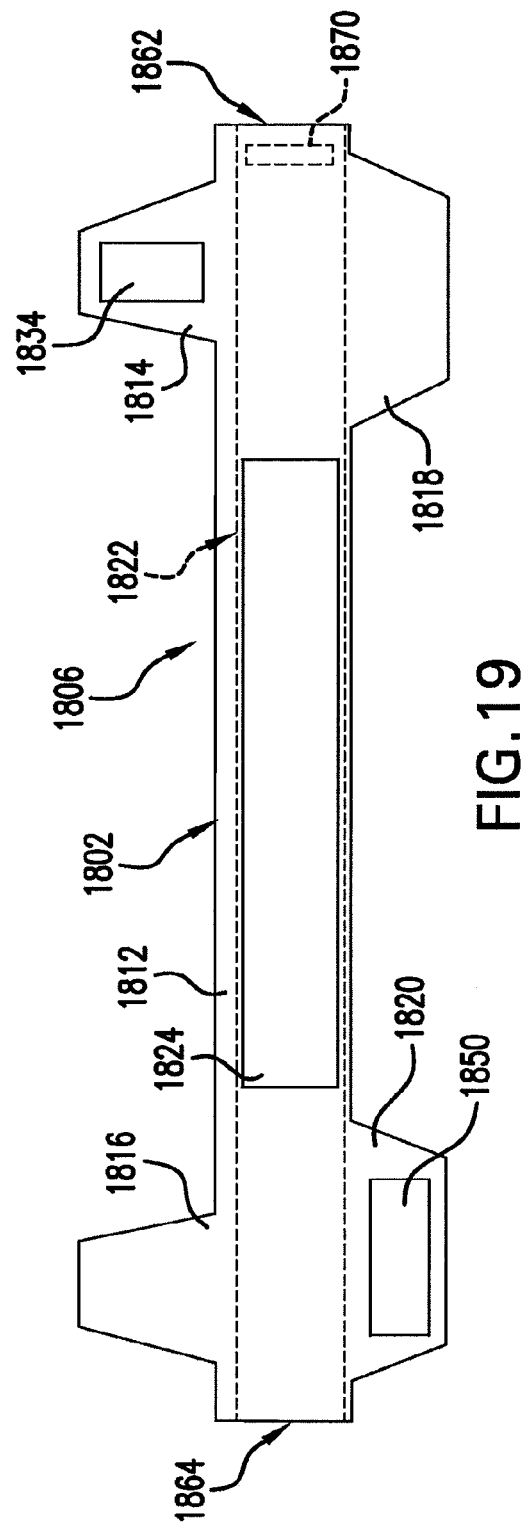
FIG. 18
FIG. 19

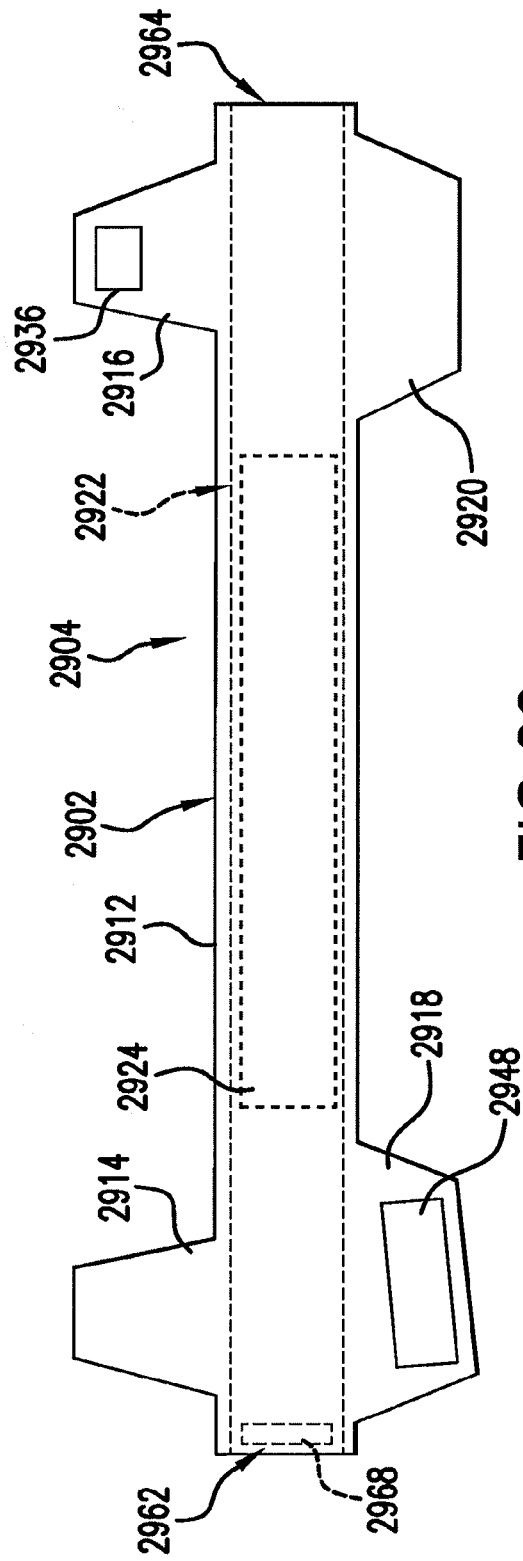
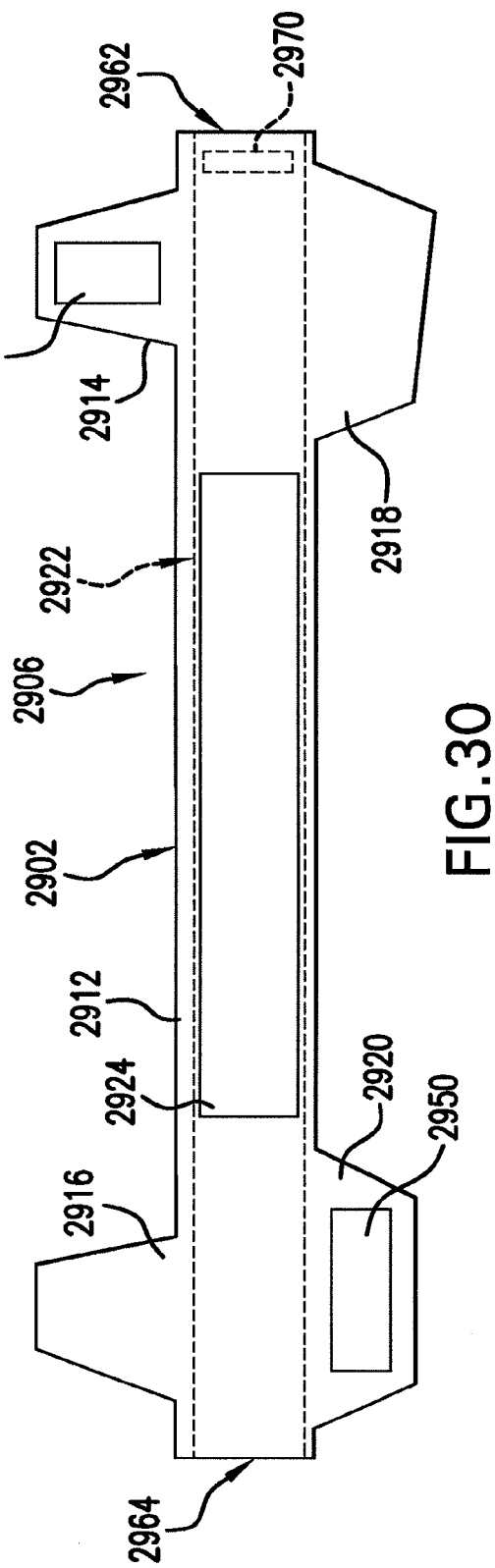

SLIPPER-LIKE DEVICE TO PREVENT OR HELP HEAL PRESSURE ULCERS OF THE FOOT

CROSS-REFERENCE TO RELATED APPLICATIONS

This application claims benefit of priority to U.S. Provisional Patent Application No. 61/293,510 to Kaminski, entitled "A SLIPPER-LIKE DEVICE TO PREVENT OR HELP HEAL PRESSURE ULCERS OF THE FOOT," filed Jan. 8, 2010, which is incorporated herein by reference in its entirety.

FIELD OF THE INVENTION

The present invention relates to a foot garment device to prevent or help prevent or heal pressure ulcers of the foot.

BACKGROUND

A pressure ulcer is created when the skin over a bony prominence is allowed to remain squeezed between that protruding hard anatomy and a firm surface for an extended period of time. The pressure can be as little as 32 mmHg (or the pressure that can be created by firmly squeezing a forefinger and thumb together to create a white print on the squeezed surface of the skin that is visible when the forefinger and thumb are separated again). The time it takes to start an injury may be as little as 20-30 minutes. When circulating blood, which gives the pink color to a individual's fingertips, is prevented from flowing, a clot may form in tiny vessels in the dermis just under the surface of the skin.

The dermis is the second of two layers of the skin. The first layer of the skin above the dermis is called the epidermis. Stopping the blood flow in the dermis deprives the overlying epidermis of the skin of oxygen and nutrients, thereby causing it to die. Repeated prolonged pressure will cause this process to extend to deeper tissues causing the necrosis (death) of the fat, muscle and bone trapped between the protuberant bone and underlying surface.

On the foot, there is little to no cushioning layer of fat, as evidenced by the fact that bones can be easily felt just below the surface of the skin. Because of this lack of a cushioning layer, pressure ulcers can form quickly and extend to the bone with the first episode of prolonged unrelieved pressure. A patient immobilized on a firm surface, even on a hospital mattress designed to lessen surface pressure, will form a clotted capillary network in the dermis at the area of continued pressure over a relatively short period of time.

There are four (4) stages assigned to pressure ulcers, depending on the depth of the necrotic tissue: In Stage I, the capillary bed under the skin surface clots and a red patch develops which cannot be blanched with finger pressure to the center of the reddish blotch. In Stage II, the epidermis overlying the clotted capillary network in the dermis dies and separates causing a blister like wound. In Stage III, the depth of the dead tissue extends through the layers of the skin into the fat beneath. In the foot, there is usually little to no fat under the skin, so these ulcers immediately become Stage III or IV and are classed "unstageable" in feet. Infection of the wound is common in Stage III and Stage IV pressure ulcers, which causes the tissues to turn dark and form a soupy drainage giving off an odor of decaying flesh.

SUMMARY

According to a first broad aspect of the present invention, there is provided a device comprising: a foot garment comprising: a bumper for positioning around and below an ankle of an individual, and one or more upper adjustable flaps and one or more lower adjustable flaps for securing the foot garment to a foot of the individual, wherein the bumper comprises a hollow sleeve for receiving padding therein, wherein the one or more lower adjustable flaps comprise a device sole when the foot garment is secured to the foot of the individual, and wherein the one or more upper adjustable flaps wrap around a top of the foot of the individual when the foot garment is secured to the foot of the individual.

According to a second broad aspect of the present invention, there is provided a method comprising: (a) providing a foot garment comprising: a bumper for positioning around and below an ankle of an individual, and one or more upper adjustable flaps and one or more lower adjustable flaps for securing the foot garment to a foot of the individual, and (b) securing the foot garment to the foot of the individual, wherein the bumper comprises a hollow sleeve and padding therein, wherein the one or more lower adjustable flaps comprise a device sole when the foot garment is secured to the foot of the individual, and wherein the one or more upper adjustable flaps wrap around a top of the foot of the individual when the foot garment is secured to the foot of the individual.

BRIEF DESCRIPTION OF THE DRAWINGS

The invention will be described in conjunction with the accompanying drawings, in which:

FIG. 1 is a schematic drawing of a dorsal or top side of a foot garment device according to one embodiment of the present invention;

FIG. 2 is a schematic drawing of a plantar or sole side of the foot garment device of FIG. 1;

FIG. 18 is a schematic drawing of a dorsal side of a foot garment device according to one embodiment of the present invention;

FIG. 19 is a schematic drawing of a plantar side of the foot garment device of FIG. 18 showing a fleece cushioning pad mounted on the bumper;

FIG. 29 is a schematic drawing of a dorsal side of a foot garment device according to one embodiment of the present invention;

FIG. 30 is a schematic drawing of a plantar side of the foot garment device of FIG. 29 showing a fleece cushioning pad mounted on the bumper;

DETAILED DESCRIPTION

Figure 3:
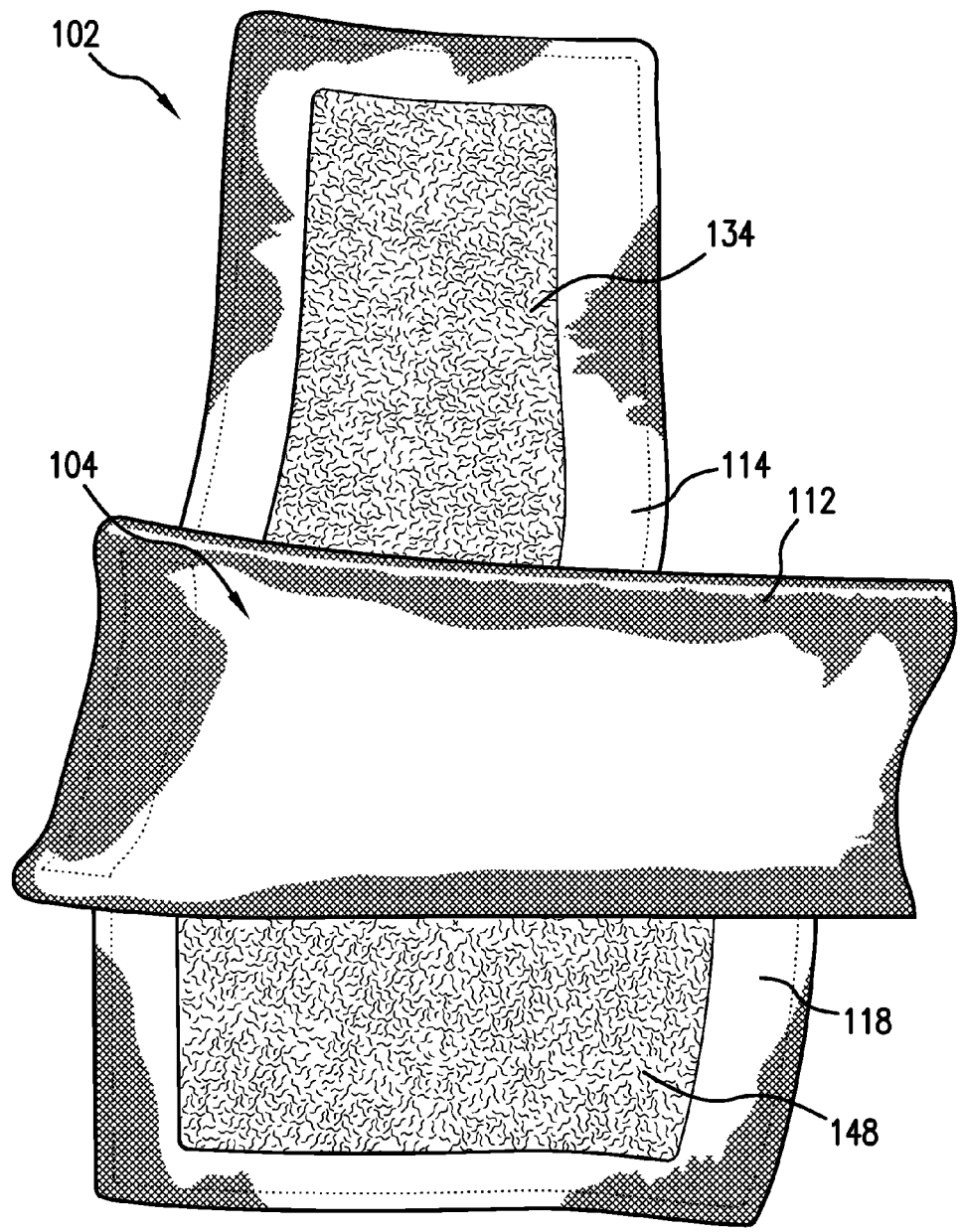
FIG. 3 is a dorsal or top side drawing of a recloseable end of the foot garment device of FIG. 1.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For purposes of the present invention, it should be noted that the singular forms, "a," "an," and "the" include reference to the plural unless the context as herein presented clearly indicates otherwise.

For the purposes of the present invention, the term "adjustable flap" refers to a flap that that may be releasably engaged to another flap or other components at two or more positions. An example of an adjustable flap is a flap that includes a strip of a hook-and-loop fastening system that may releasably engage another strip of the hook-and-loop fastening system on another flap or other component of a foot garment. An adjustable flap may also include: a series of openings for releasably engaging one or more buttons on another flap or other component of a foot garment, a single opening for releasably engaging two or more buttons on another flap or other component of a foot garment, a series of buttons for releasably engaging one or more openings on another flap or other component of a foot garment, a single button for releasably engaging two or more openings on another flap or other component of a foot garment, a series of snaps for releasably engaging one or more snaps on another flap or other component of a foot garment, a single snap for releasably engaging two or more snaps on another flap or other component of a foot garment, etc.

For the purposes of the present invention, the term "dorsal" refers to the top of a foot or to the direction away from the skin top of the foot over which a foot garment device of the present invention is secured to form the upper flap of the slipper-like foot garment device of the present invention.

For the purposes of the present invention, the term "plantar" or "bottom of a foot" refers to the direction towards the skin of the foot to which a foot garment device of the present invention is secured, i.e., when in the standing position the plantar surface rests against the floor.

For the purpose so the present invention, the term "releasably engage" refers to two components, such as two flaps, that are engaged to each other by a fastening system that allows the components to be unfastened from each other with relatively little force. Examples of such fastening systems are hook-and-loop fasteners, button-and-hole fasteners, snap fasteners, etc.

For the purposes of the present invention, the term "removable padding" refers to padding that is not permanently attached to a hollow sleeve of the present invention by sewing the padding to the hollow sleeve, adhering the padding to the hollow sleeve, etc. In some applications, it may not be desirable to remove removable padding from a hollow sleeve. In other applications, it may be desirable to remove the removable padding to allow the padding to be altered to better conform to the anatomy of an individual's foot. In yet other applications, it may be desirable to remove removable padding to replace the padding with other removable padding. Removable padding may be held in place in a hollow sleeve by providing a reclosable seal at an open end of the hollow sleeve or by sewing closed an open end of the hollow sleeve after inserting the removable padding in the hollow sleeve.

For the purposes of the present invention, the term "Velcro® strip" refers to a strip of any hook-and-loop fastener, such as a strip of Velcro® manufactured by Velcro Industries. A Velcro® strip refers to a strip including either the hooks or loops of a Velcro® hook-and-loop fastener. A Velcro® hook-and-loop fastener includes one strip of hooks and one strip of loops that releasably engage each other. In general it is desirable that the strip of hooks of the Velcro® strips faces away from the skin when the foot garment is secured to the foot of an individual. Other suitable similarly functioning material might be used.

Description

There is currently no foot garment device this small that reliably stays in place and relieves pressure over all the bony prominences of the foot. Current foot garment devices are also "one size fits all" types that may not be readily adapted to the particular anatomy of an individual's foot.

Current foot garment devices are generally one of two types. The first type of device is a padded cup that is placed over the heel. Such devices may protect the skin, but do not relieve pressure. The second type of device is a ski boot-like design with a space cut into the rear and/or is fitted with a firm arch extending upward from the sole so as to float he heel but is so bulky that the patient cannot easily walk in it or wear the device in bed. This second type of foot garment device immobilizes the patient and places other areas of the anatomy where bones are near the surface at increased risk of forming pressure ulcers. For most patients, these boot-like devices are so loose that pressure relief fails because the foot twists within it. The usual response of the caregiver staff is to excessively tighten the device around the foot. This often creates different areas of pressure causing new wounds due to the pressure-relieving boot itself, especially when the straps are tightened across the dorsum of the foot.

In one embodiment, the foot garment device of the present invention is designed to be adaptable to float the protuberant anatomy of an individual's foot. The bony excrescences of the foot include the heel as well as the metacarpal phalangeal (MP) joint on the medial side of the foot (the bunion area) and two protrusions on the lateral side of the foot. These are the MP joint of the little toe and the metacarpal tarsal joints around the mid-lateral side of the foot. The unique features of the foot garment device of the present invention provide the advantages of: being comfortable to wear, allowing the patient to turn in bed to sleep on one side or the other, staying in place and even allowing the patient to walk short distances while wearing the device. In one embodiment of the present invention, by arranging the dorsal and plantar Velcro® straps, the foot garment device may be made relatively small or large.

The foot garment device of the present invention gently secures the foot, beginning at the Achilles tendon at the back of the foot, and wrapping around both sides of the foot in the natural groove formed below by the heel bone (calcaneous) and the ankle bones above (lateral and medial malleolius). In one embodiment, the foot garment device, which contains a bumper that conforms to this natural groove in the foot, wraps around an individual's foot so that the bony protuberant anatomy of the individual's foot floats off the underlying surface. The flap/Velcro® dorsum of the foot garment device keeps the ankle seated against the back of the device and prevents the heel from touching the under surface, no matter the angle at which an individual's foot rests while lying down.

In one embodiment, the foot garment device is a slipper-like device. In one embodiment the bumper comprises a pocket or sleeve sewn into the foot garment that holds batting stuffed into the sleeve, an elongated member of a conformable soft material such as a foam material tube, a foam material cylinder, etc., inserted into the sleeve, or another type of padding stuffed or inserted into the sleeve. The foam material tube or cylinder may be made of a flexible foam material. Examples of flexible foam materials that may be used in the foam material tube include polyurethane foam rubber, latex foam rubber, etc. In one embodiment, if a foam material tube or cylinder is used, two diamond-shaped hinge cuts may be made at the back of the tube or cylinder so that when the tube is folded around the protruding ankle bones above and the heel below, the tube gently grips the foot and floats all prominent bony anatomy off the underlying surface. Although diamond-shaped hinge cuts are one suitable shape of the hinge cuts, other shapes such as grooves, ovals, circles, etc. may be employed in some embodiments of the present invention. Also, in some embodiments of the present invention, instead of hinge cuts, the foam material cylinder or tube may be molded or otherwise preformed to include hinge recesses or hinge grooves that function similarly to hinge cuts. In addition to a hollow tube or cylinder, the elongated member of conformable soft material may have other shapes. For example, the elongated member may have rounded or tapered ends, may have an oval or contoured cross-section instead of a circular cross-section, may have a different cross-sectional shape and/or different-sized diameter at different points along the length of the member, etc.

In one embodiment, the elongated member comprising a foam material may comprise a memory foam material, such as a visco-elastic polyurethane foam. In such an embodiment, instead of hinge cuts, the elongated member comprising memory foam may be molded or otherwise preformed to include hinge recesses or hinge grooves that function similarly to hinge cuts.

In one embodiment of the present invention, the foot garment device is secured to the foot of an individual using one or more adjustable upper flaps and one or more adjustable lower flaps that wrap around the top and sole of the foot, respectively. In one embodiment, when two adjustable upper flaps are used, the adjustable upper flaps are releasably fastened to each other by releasably engaging fasteners. In one embodiment, when two adjustable lower flaps are used, the adjustable lower flaps are releasably fastened to each other by releasably engaging fasteners. In one embodiment when a single adjustable upper flap is used, the adjustable upper flap may be releasably fastened to the hollow sleeve. In one embodiment when a single adjustable lower flap is used, the adjustable lower flap may be releasably fastened to the hollow sleeve. In other embodiments three or more upper and/or lower flaps may be used.

The foot garment device may be made of a fabric material such as flannel, velvet, terry cloth, silk, fleece, etc. The fabric material may be natural or synthetic. The material used for the sleeve may be the same material as used for the rest of the foot garment device or may be different.

The present invention takes advantage of the discovery that the natural groove, ankle bones above and heel below, can be used to hold a cushioning device that floats the bony anatomy (the sites of pressure) off any underlying surface that the foot is resting on, thereby preventing pressure on the skin over these sites. This customized consistent flotation protects the skin from forming an ulcer due to pressure on the skin squeezed between the bone and the underlying surface.

If an ulcer has formed due to pressure over these bony prominences the pressure relief is essential for healing, along with proper care of a wound. Therefore, in some embodiments the present invention provides a customized consistent flotation of a wound, along with its dressing, for all areas of the foot that have a pressure ulcer or are prone to a pressure ulcer.

In one embodiment of the present invention, the padding, whether a foam material tube, batting or other cushioning material, is contained in the rim of a fabric slipper-like device. Velcro fasteners allow adjustment of both the sole below and cross flap above to conform to any adult foot. Several designs may be employed to hold the cushioning material in place.

Figure 4:
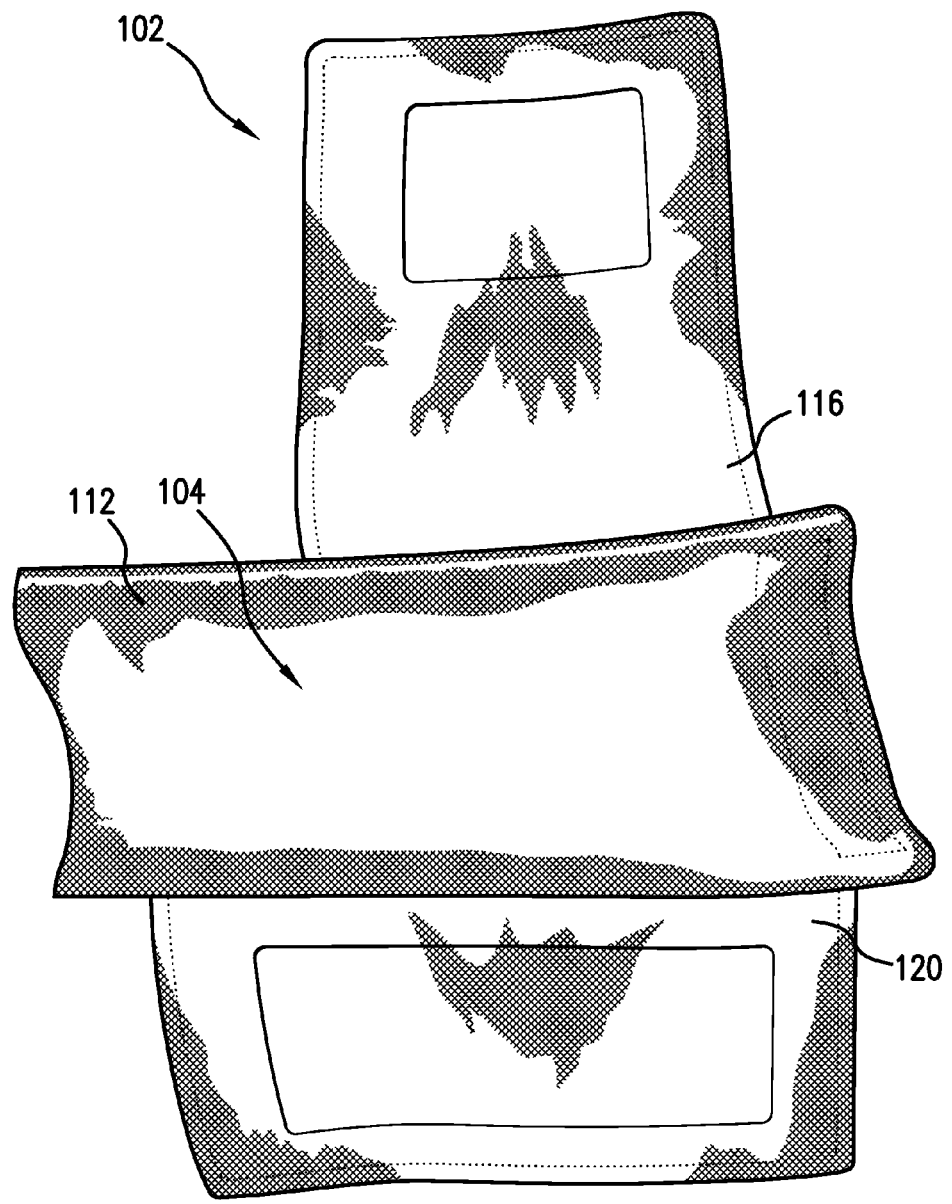
FIG. 4 is a dorsal or top side drawing of a closed end of the dorsal side of the foot garment device of FIG. 1.
Figure 5:
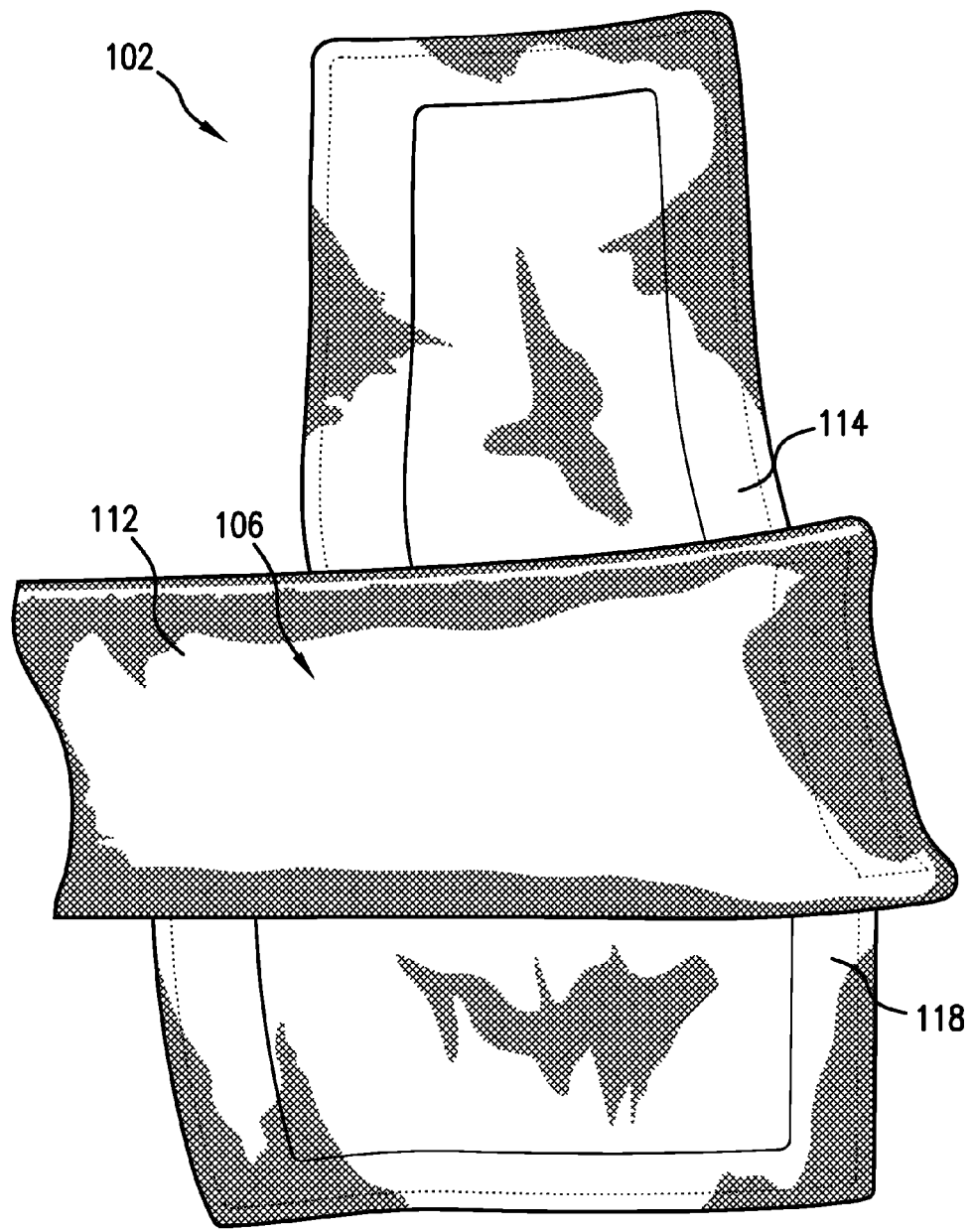
FIG. 5 is a plantar side drawing of the recloseable end of the foot garment device of FIG. 1.
Figure 6:
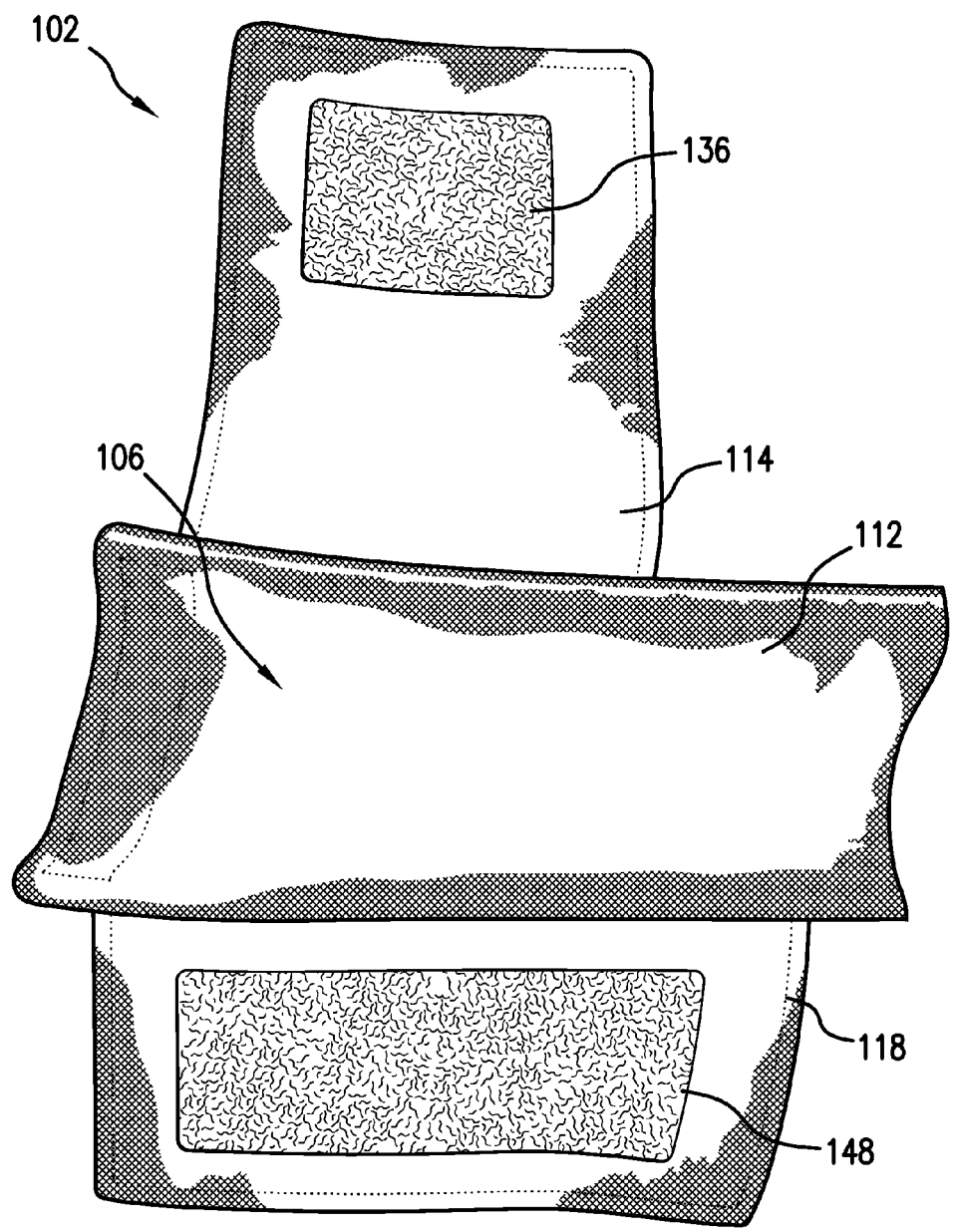
FIG. 6 is a plantar side drawing of the closed end of the foot garment device of FIG. 1.

A foot garment device 102, according to one embodiment of the present invention, is shown in FIGS. 1, 2, 3, 4, 5 and 6. FIG. 1 shows a dorsal side 104 of foot garment device 102. FIG. 2 shows a plantar side 106 of foot garment device 102. Foot garment device 102 includes a bumper 112, adjustable upper flaps 114 and 116 and adjustable lower flaps 118 and 120. Bumper 112 comprises a hollow sleeve 122 in which is inserted a foam material tube 124 shown by dashed lines in FIGS. 1 and 2. Upper flaps 114 and 116 include respective Velcro® strips 134 and 136 that may be releasably engaged to each other to form an upper strap that wraps around the top of an individual's foot to which foot garment device is secured. As shown in FIGS. 1 and 2, Velcro® strip 134 is on dorsal side 104 and Velcro® strip 136 is on plantar side 106 of foot garment device 102. Lower flaps 118 and 120 include respective Velcro® strips 148 and 150 that may be releasably engaged to each other to form a device sole (not shown in FIGS. 1 and 2) that wraps around the sole of the foot of the individual (not shown in FIGS. 1 and 2). As shown in FIGS. 1 and 2, Velcro® strip 148 is on dorsal side 104 and Velcro® strip 150 is on plantar side 106 of foot garment device 102. An open end 162 of sleeve 122 is open to allow foam material tube 124 to be inserted into sleeve 122. Sleeve 122 also includes a closed end 164. Open end 162 may be releasably closed by Velcro® strips 168 and 170, shown by dashed lines, on opposite sides of the interior of open end 162 of sleeve 122. Open end 162 is also shown in FIGS. 3 and 5. Open end 164 is also shown in FIGS. 4 and 6.

In the embodiment shown in FIGS. 3, 4, 5 and 6, Velcro® strips 136 and 150 are abrasive hooks and Velcro® strips 134 and 154 are loops. Therefore, the hooks will face away from the skin of the foot when foot garment device 102 is secured to the foot of an individual. This will prevent the hooks from irritating the foot. However, in other embodiments of the present invention strip 136 and/or strip 150 may be loops and strip 134 and/or strip 150 may be hooks.

Figure 7:
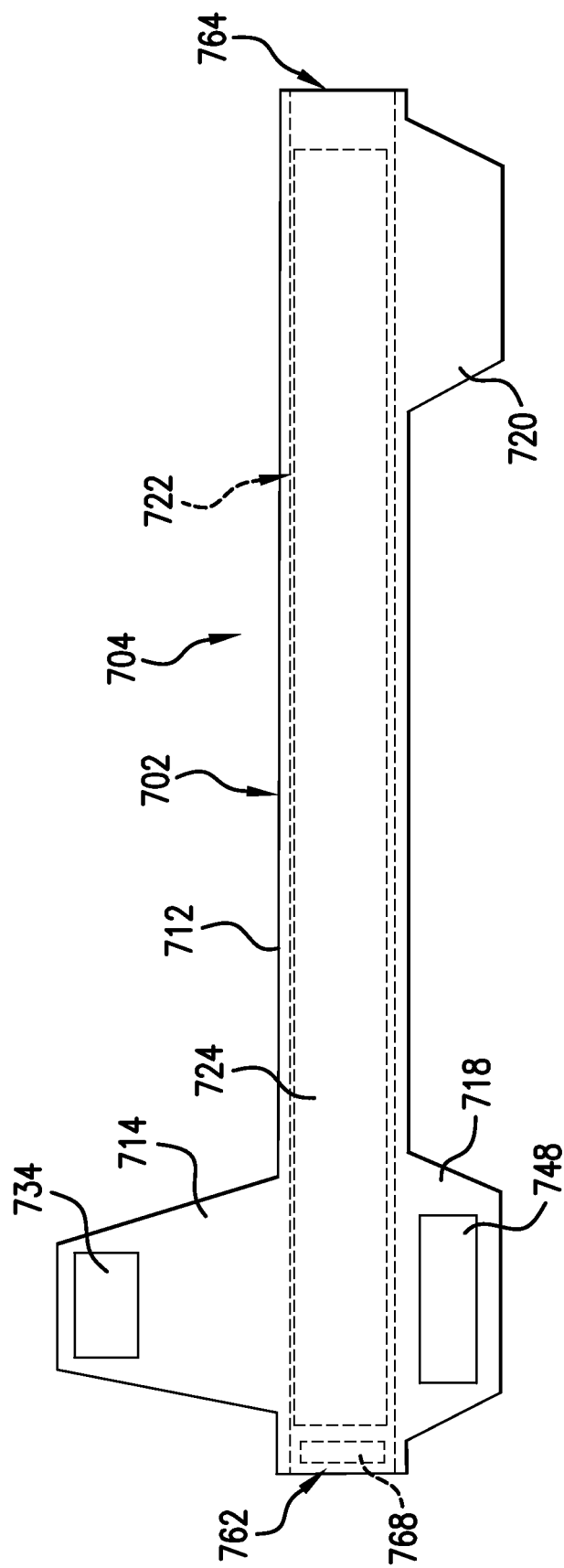
FIG. 7 is a schematic drawing of a dorsal or top side of a slipper-like foot garment device according to one embodiment of the present invention.
Figure 8:
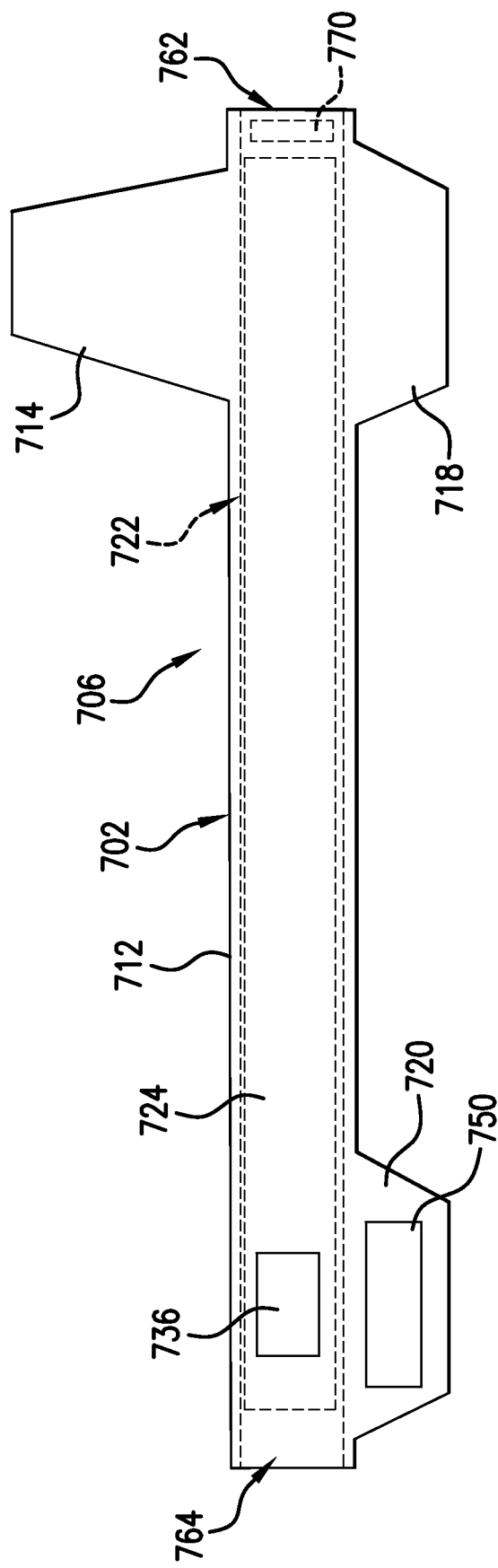
FIG. 8 is a schematic drawing of a plantar or sole side of the slipper-like foot garment device of FIG. 7.
Figure 9:
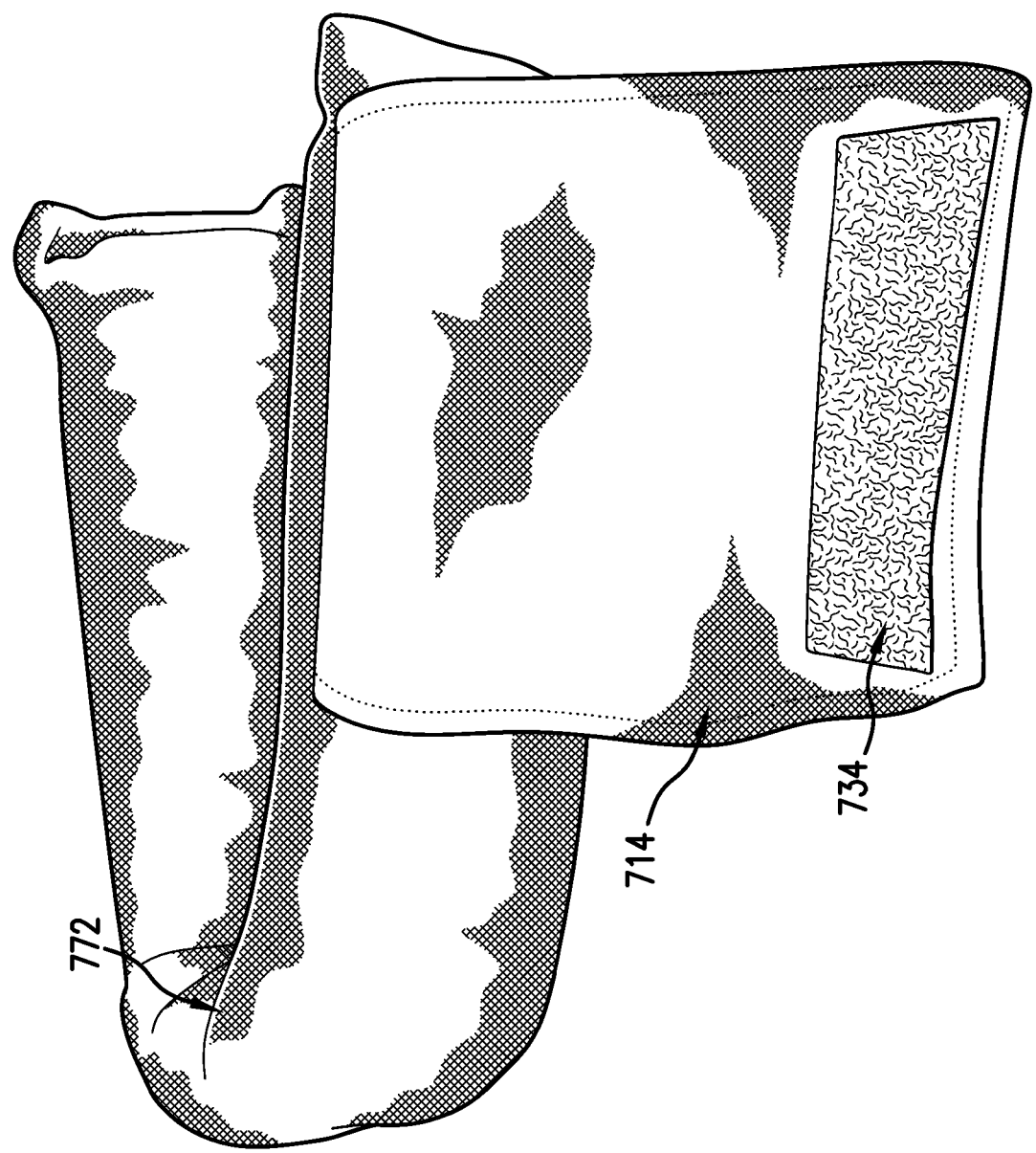
FIG. 9 is a perspective view drawing from the side of the slipper-like foot garment device of FIG. 7 with a top flap in an open position; i.e., the Velcro® strip of the top flap is not secured to a Velcro® strip (not visible in FIG. 9) on a bumper of the foot garment device.
Figure 10:
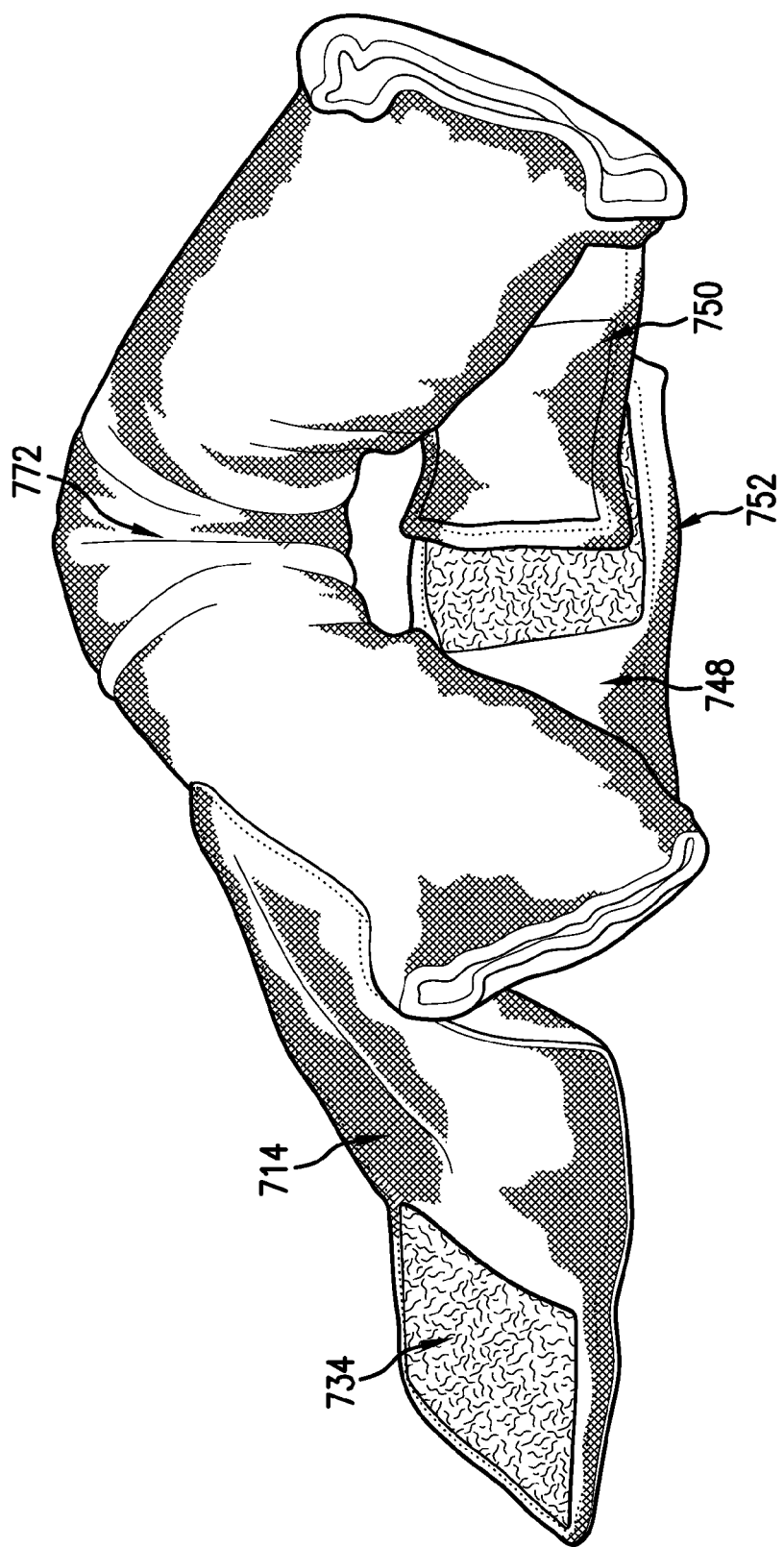
FIG. 10 is a plantar side drawing of the foot garment device of FIG. 9 with the lower flaps secured to each other to form a lower strap or sole of the slipper-like foot garment device.
Figure 11:
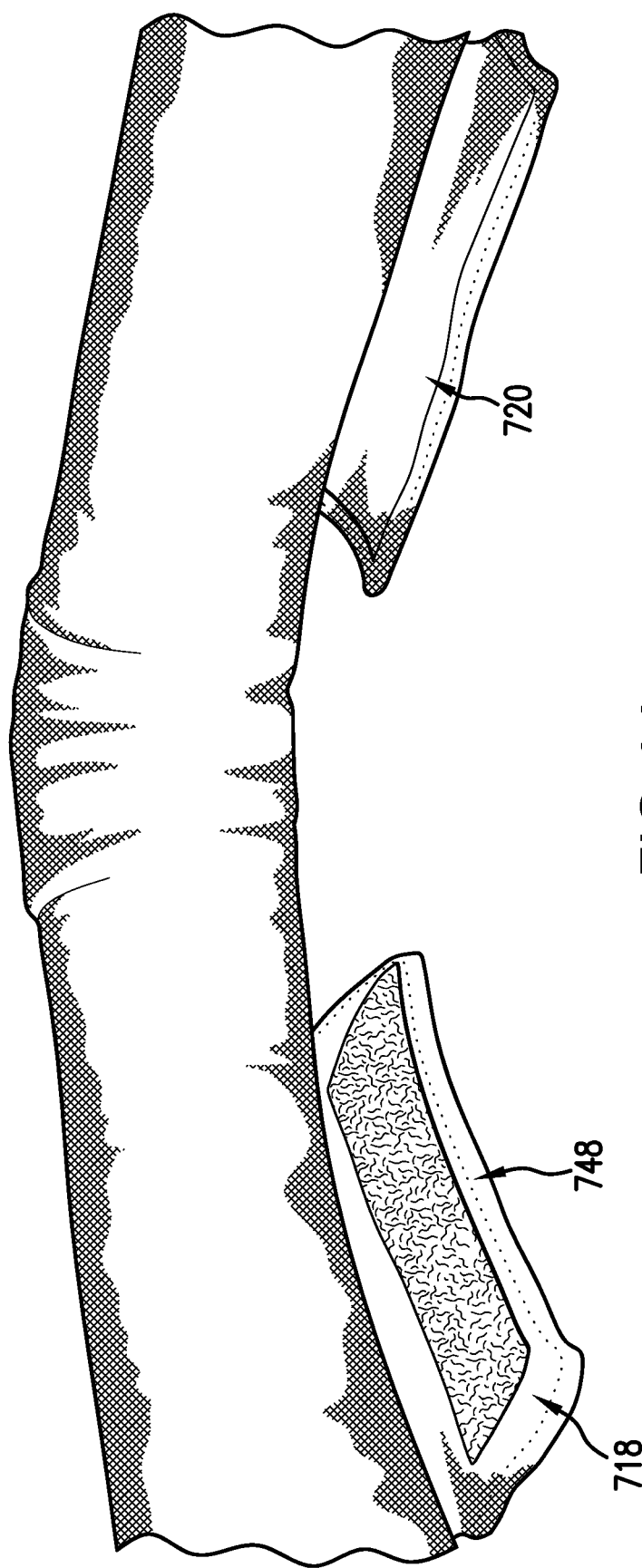
FIG. 11 is a plantar side drawing of the foot garment device of FIG. 9 with the lower flaps open; i.e., not secured to each other.
Figure 12:
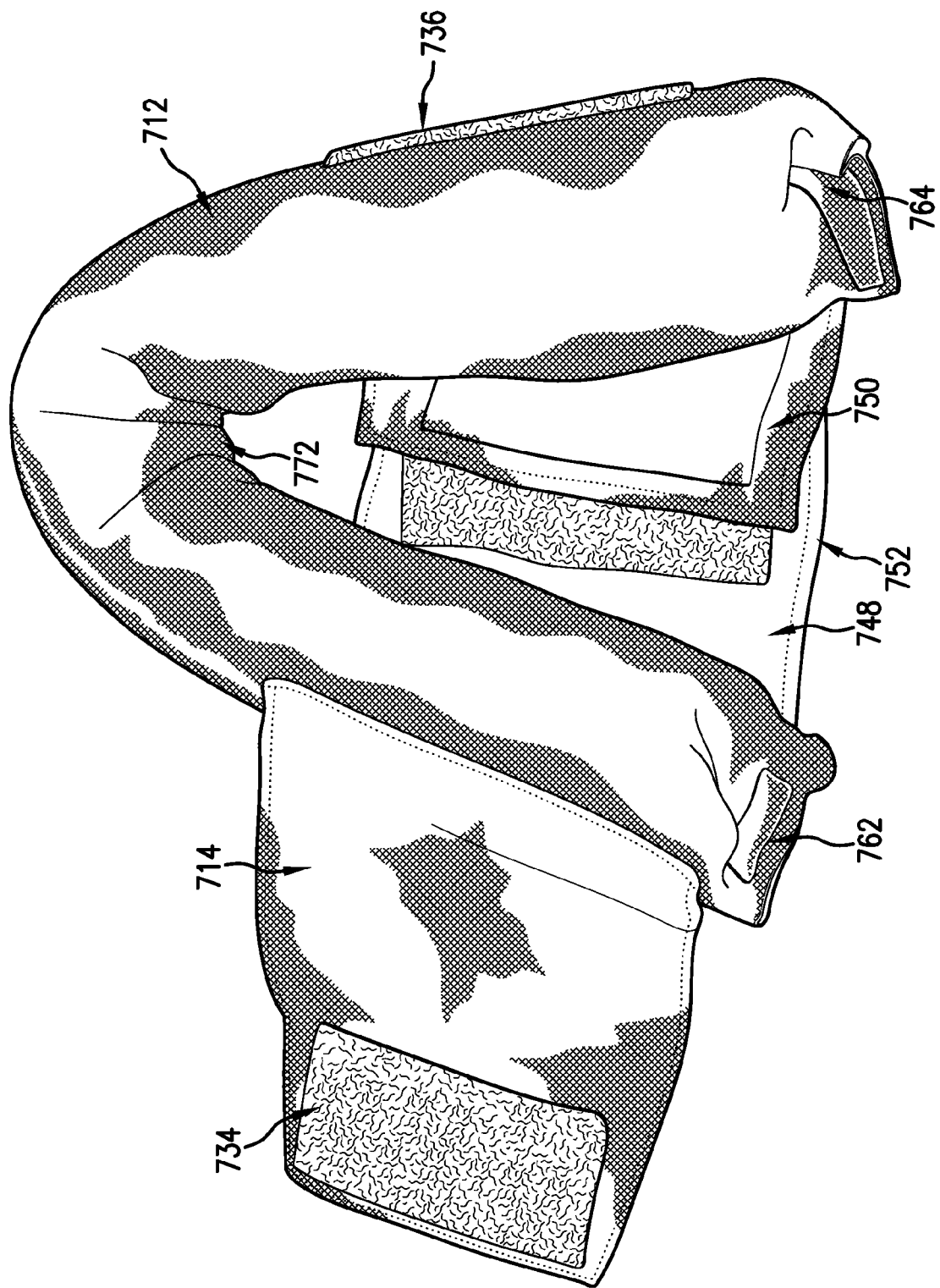
FIG. 12 is a drawing of the top foot garment device of FIG. 9 with the lower flaps secured to each other to form a lower strap, thereby forming a sole of the slipper-like foot garment device and with the top flap in an open position.
Figure 13:
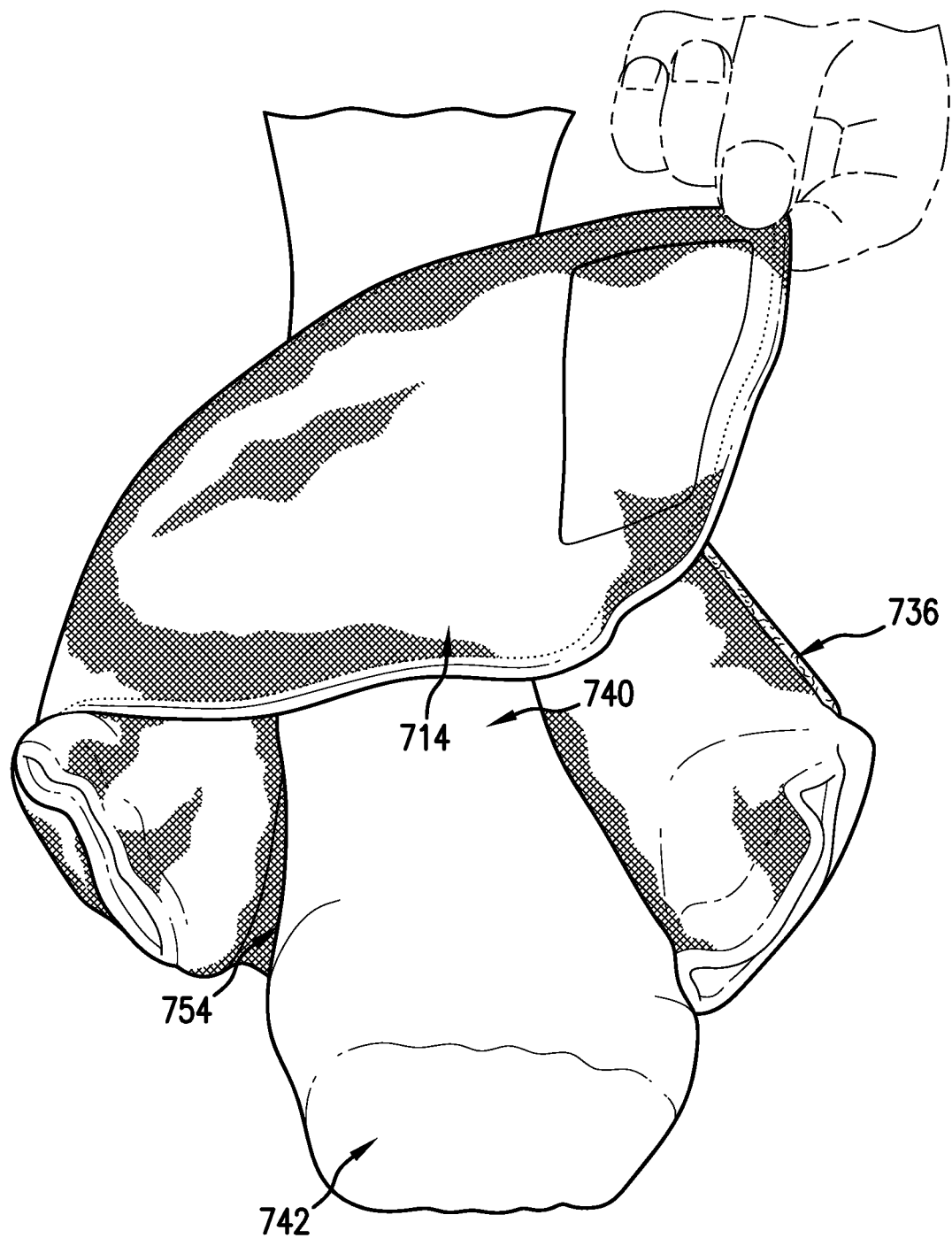
FIG. 13 is a drawing of the foot garment device of FIG. 9 being secured to a (left) foot of an individual wearing a sock by wrapping the upper flap around the top of the foot.
Figure 14:
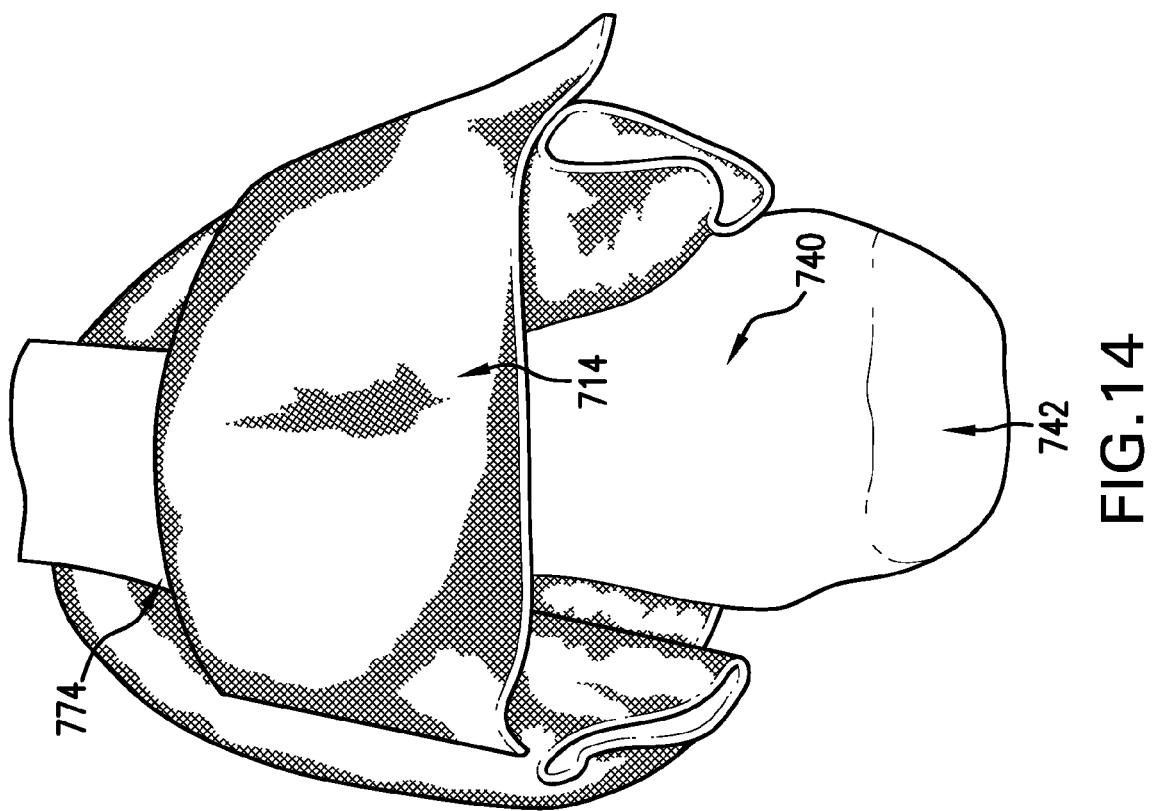
FIG. 14 is a drawing of the foot garment device of FIG. 13 with the upper flap in a closed position; i.e., secured to the Velcro® strip (not visible in FIG. 14) on the bumper of the foot garment device.

A foot garment device 702 according to one embodiment of the present invention is shown in FIGS. 7, 8, 9, 10, 11, 12, 13, 14, 15, 16 and 17. FIG. 7 shows a dorsal side 704 of foot garment device 702. FIG. 8 shows a plantar side 706 of foot garment device 702. Foot garment device 702 includes a bumper 712, adjustable upper flap 714 and adjustable lower flaps 718 and 720. Bumper 712 comprises a hollow sleeve 722 in which is inserted a foam material tube 724 shown by dashed lines in FIGS. 7 and 8. Upper flap 714 includes a Velcro® strip 734 that may be releasably engaged to a Velcro® strip 736 on bumper 712 so that upper flap 714 wraps around a top 740 of a foot 742 to which foot garment device 702 is secured, as shown in FIGS. 13 and 14. As shown in FIGS. 7 and 8, Velcro® strip 734 is on dorsal side 704 and Velcro® strip 736 is on plantar side 706 of foot garment device 702. Lower flaps 718 and 720 include respective Velcro® strips 748 and 750 that may be releasably engaged to each other to form a device sole 752 that wraps around sole 754 of foot 742 as shown in FIGS. 10, 12, 13 and 15. As shown in FIGS. 7 and 8, Velcro® strip 748 is on dorsal side 704 and Velcro® strip 750 is on plantar side 706 of foot garment device 702. An open end 762 of sleeve 722 is open to allow foam material tube 724 to be inserted into sleeve 722. Open end 762 may be closed by Velcro® strips 768 and 770, shown by dashed lines, on opposite sides of the interior of end 762 of sleeve 722. Closed end 764 of sleeve 722 is sewn closed.

In one embodiment of the present invention, shown in FIGS. 9-17, Velcro® strips 734 and 750 are hooks and Velcro® strips 736 and 748 are loops. Because Velcro® strips 734 and 750 are hooks and, therefore, are abrasive, Velcro® strips 734 and 750 will face away from the skin of the foot when foot garment device 702 is secured to the foot.

Figure 15:
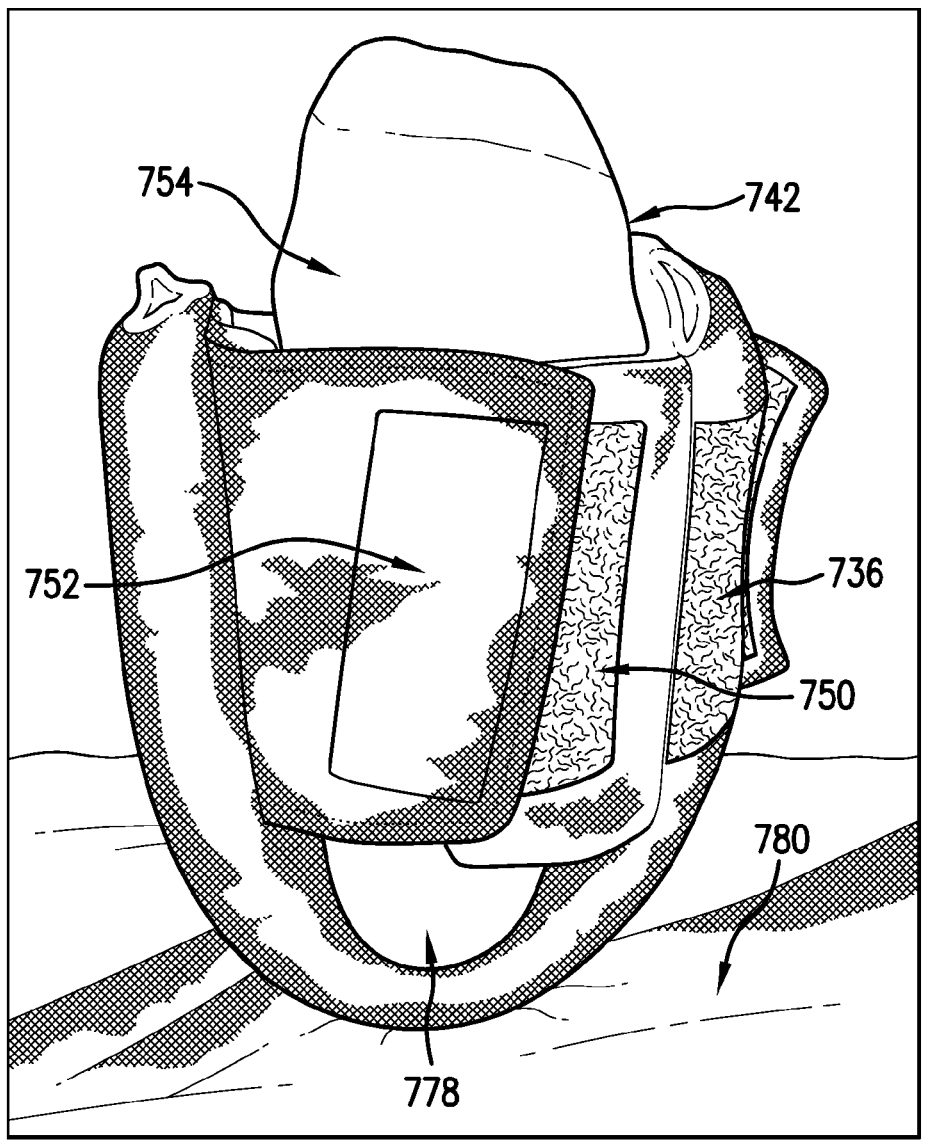
FIG. 15 is a drawing of the bottom of foot garment device of FIG. 14, with the foot lying on its heel, showing how the heel of the foot to which the foot garment device is secured "floats" above a surface upon which the heel of the foot would otherwise rest.
Figure 16:
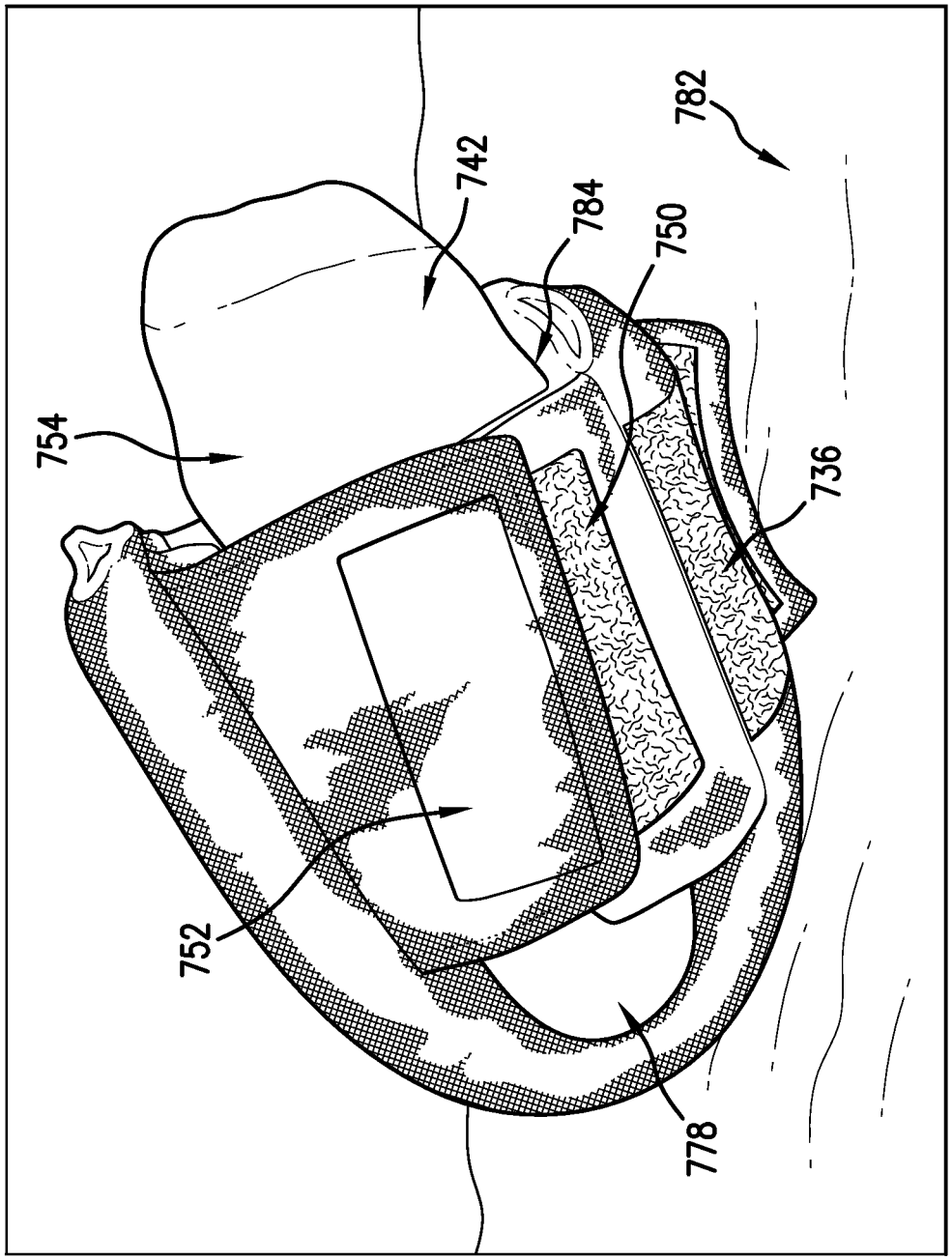
FIG. 16 is a drawing of the bottom of the foot and foot garment device of FIG. 15, with the foot lying on its left/outer side, showing how the bony prominences of this side of the foot "float" above a surface upon which they would otherwise rest due to the foot garment device being secured to the foot.
Figure 17:
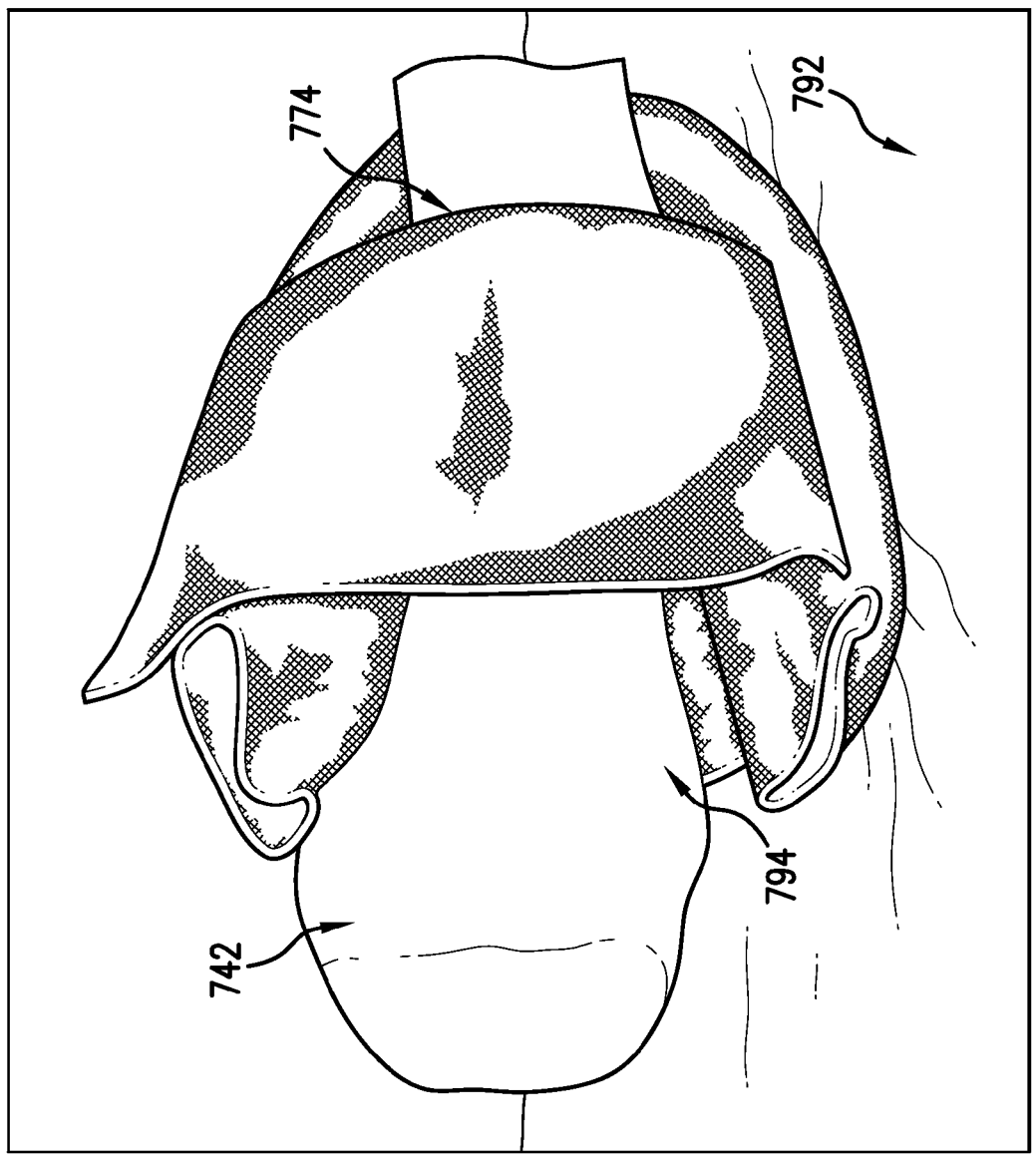
FIG. 17 is a drawing of the top of foot and foot garment device of FIGS. 15 and 16, with the foot resting on its right/inner side, showing how the side of the foot "floats" above a surface upon which the foot would otherwise rest due to the foot garment device being secured to the foot.

FIGS. 9, 10, 11, 12, 14 and 15 show foot garment device 702 with bumper 712 bent around to include a bend 772 so that foot garment device 702 may be placed around the back of foot 742 and beneath an ankle 774. FIGS. 13 and 14 illustrate flap 714 being secured across top 740 of foot 742. FIG. 15 shows how heel 778 of foot 742 "floats" above a surface 780, such as a cushion or bed, upon which foot 742 would otherwise rest due to foot garment device 702 being secured to foot 742. FIG. 16 shows how the left lateral decubitus, lateral foot/mp and MT joint of foot 742 "float" above a surface 782, such as a cushion or bed, upon which left side/outer side 784 of foot 742 would otherwise rest due to foot garment device 702 being secured to foot 742. FIG. 17 shows how the right lateral decubitus and medial foot/bunion of foot 742 "float" above a surface 792, such as a cushion or bed, upon which right side/inner side 794 of foot 742 would otherwise rest due to foot garment device 702 being secured to foot 742.

A foot garment device 1802, according to one embodiment of the present invention, is shown in FIGS. 18 and 19. FIG. 18 shows a dorsal side 1804 of foot garment device 1802. FIG. 19 shows a plantar side 1806 of foot garment device 1802. Foot garment device 1802 includes a bumper 1812, adjustable upper flaps 1814 and 1816 and adjustable lower flaps 1818 and 1820. Bumper 1812 comprises a hollow sleeve 1822 in which is inserted foam material tube (not shown in FIGS. 18 and 19). Mounted on plantar side 1806 of bumper 1812 is a fleece cushioning pad 1824. Upper flaps 1814 and 1816 include respective Velcro® strips 1834 and 1836 that may releasably engaged to each other to form an upper strap that wraps around the top of an individual's foot to which foot garment device 1802 is secured. As shown in FIGS. 18 and 19, Velcro® strip 1834 is a strip of hooks and is located on dorsal side 1804 of foot garment device 1802. Velcro® strip 1836 is a strip of loops and is located on plantar side 1806 of foot garment device 1802. Lower flaps 1818 and 1820 include respective Velcro® strips 1848 and 1850 that may be releasably engaged to each other to form a device sole (not shown in FIGS. 18 and 19) that wraps around the sole of the foot of the individual. As shown in FIGS. 18 and 19, Velcro® strip 1848 is a strip of hooks on dorsal side 1804, and Velcro® strip 1850 is a strip of loops on plantar side 1806 of foot garment device 1802. Open end 1862 of sleeve 1822 is open to allow the foam material tube (not shown in FIGS. 18 and 19) to be inserted into sleeve 1822. Closed end 1864 of sleeve 1822 is sewn closed. Open end 1862 may be closed by Velcro® strips 1868 and 1870, shown by dashed lines, on opposite sides of the interior of end 1862 of sleeve 1822.

As shown in the embodiment of FIGS. 18 and 19, a Velcro® strip including hooks may be smaller than the Velcro® strip including loops. Also, although particular combinations of Velcro® strips of hooks and loops are shown in FIGS. 18 and 19, the flap and side including strips or loops may be different in different embodiments of the present invention. In one embodiment of the present invention the strip of hooks on the upper flap may be about 1.5 inches in height by about 2 inches in width and the mating strip of loops may be about 3.5 inches in height by about 2 inches in width. In one embodiment of the present invention, the Velcro® strips on the lower flaps may be 2 inches in height by 4 inches in width.

In one embodiment of the present invention, the fleece cushioning pad of FIGS. 18 and 19 may be about 2 inches in height by about 8 inches in width. In one embodiment, the bumper may be about 3.5 inches in height by about 21 inches in length. The upper flaps may be about 4 inches in width at their base, where they join the bumper, and about 3.5 inches in width at their tops and about 4 inches in height. The lower flaps may be about 6 inches in width at their base, wherein they join the bumper, and about 5 inches in width at their tops and about 2.25 inches in height. The distance between the upper flaps along the bumper may be about 11 inches and the distance between the lower flaps along the bumper may be about 8.25 inches. However, other embodiments of the present invention may have different dimensions.

Some embodiments of the foot garment devices of the present invention are easy to apply and adjust to an adult foot size by adjusting the size of the upper strap and device sole using the upper and lower flaps, respectively. Overlapping the upper flaps more and/or the lower flaps more may be done to fit a smaller foot. Conversely, overlapping the upper flaps less and/or the lower flaps less may be done to fit a larger foot.

In some embodiments of the present invention employing a foam material tube as the padding, adjustments to the foam material tube may be made to prevent pressure over a bony anatomical protrusion by the tube itself. For example, due to anatomical variation such as low positioned ankle bones or unusual foot characteristics of the MP and MT joints, as with bunions, or a deformed diabetic foot, etc., the soft padding provided by the foam material tube can be tailored. With the foot garment device on the foot, an individual, such as a physician, registered nurse, physical therapist or even patient, may run a finger between the bumper and the foot searching for any uneven pressure, especially over the underlying bony features. The foot garment may be designed so the foam material tube may be easily removed and the surface of the tube cut away to form anatomy cuts so that pressure points caused by the foam material tube are eliminated.

In one embodiment of the present invention, the foam material tube may be removable. In one embodiment, the foam material tube may be pre-cut to provide a hinge at the back to grip the Achilles tendon. In one embodiment, the foam material tube may be custom cut to provide a hinge based on the size of an ankle of the individual. In one embodiment, shown in FIGS. 20-22, the hinge may be formed by cutting out two diamond-shaped pieces side by side from the back of the tube to form hinge cuts. Also, the inner aspect of the distal ends of the foam material tube may be tapered. An anatomy cut may be cut into the medial and lateral side cushions just in front of the hinge cuts. The lateral side divot may be cut lower and the medial side anatomy cut higher, as the anatomy dictates. Before and after the foam material tube is replaced in the sleeve, the wound care technician, such as physician, registered nurse, physical therapist, etc., runs an index finger along the inside ridge of the cushioning tube and feels for any bony prominence of the foot that is touching the bumper. The tube material is removed and again cut away so these bony excrescences do not push into the bumper to the extent that the bony excrescences contact the foam material through the sleeve. The foam material tube is cut to form anatomy cuts so these bony excrescences "float" with the weight of the foot distributed along the remaining foam material padding. Particular care may be taken over the tuberosity of the 5th metatarsal and the metatarsal phalangeal joint along the lateral side of the foot. Along the medial aspect of the foot, room must be made for the 1st metatarsal phalangeal (the bunion) joint.

Once the foam material tube has been shaped as desired, the foam material tube may be placed back into the hollow sleeve. A pull-through-assist device may be attached to one end of the foam material tube for ease of replacement in pulling the foam material tube into the hollow sleeve. For example, the hollow fabric sleeve may be open at both ends and the sleeve may be held vertically. Then a pull wire attached to the foam material tube may be inserted in one open end and allowed to drop through the sleeve until the pull wire emerges at the other open end. The pull wire may then be used to pull the foam material tube into the sleeve. A pull-through assist device may also be used to assist a user in pulling the foam material tube from the hollow sleeve.

The foot surface width may be adjusted for comfortable fit using an adjustable fastener such as a Velcro® fastener along the sole of the device. The garment may then be wrapped around the foot, the top flap secured and the index finger again run inside the upper rim of the garment to be sure that there is no pressure created by any bony prominence against the fabric-wrapped foam material tube within the sleeve of the foot garment device.

The above sequence of "seeking for any area of pressure and subsequent trimming" of the tube may be repeated until all sites of focused pressure that would create wounds are free with the underlying bony anatomy cradled in a space.

Figure 20:
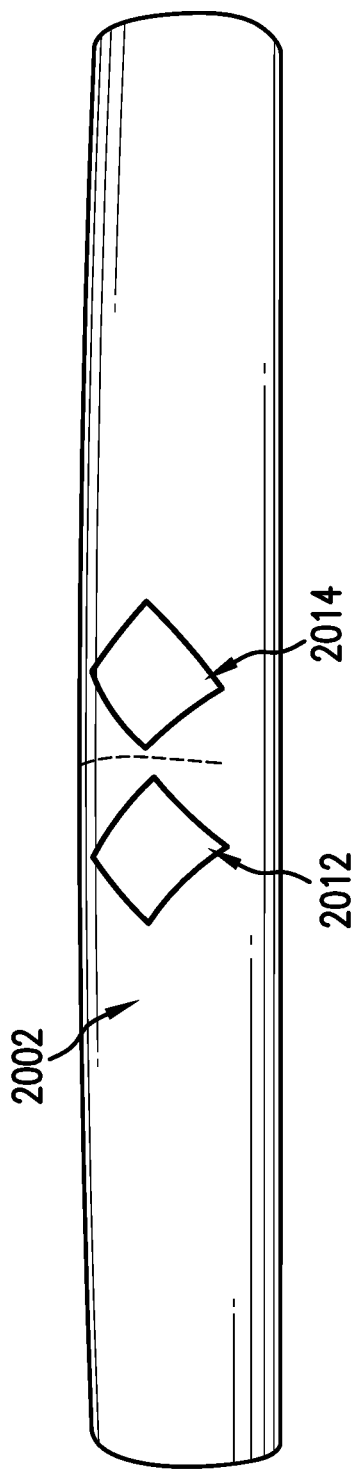
FIG. 20 is a drawing of a foam material tube that is being prepared to be placed into a sleeve of the garment to serve as a bumper for a garment device of the present invention showing where diamond-shaped hinge cuts will be made to assist the tube in bending/crimping more readily about the Achilles tendon, thereby securing it in place.
Figure 21:
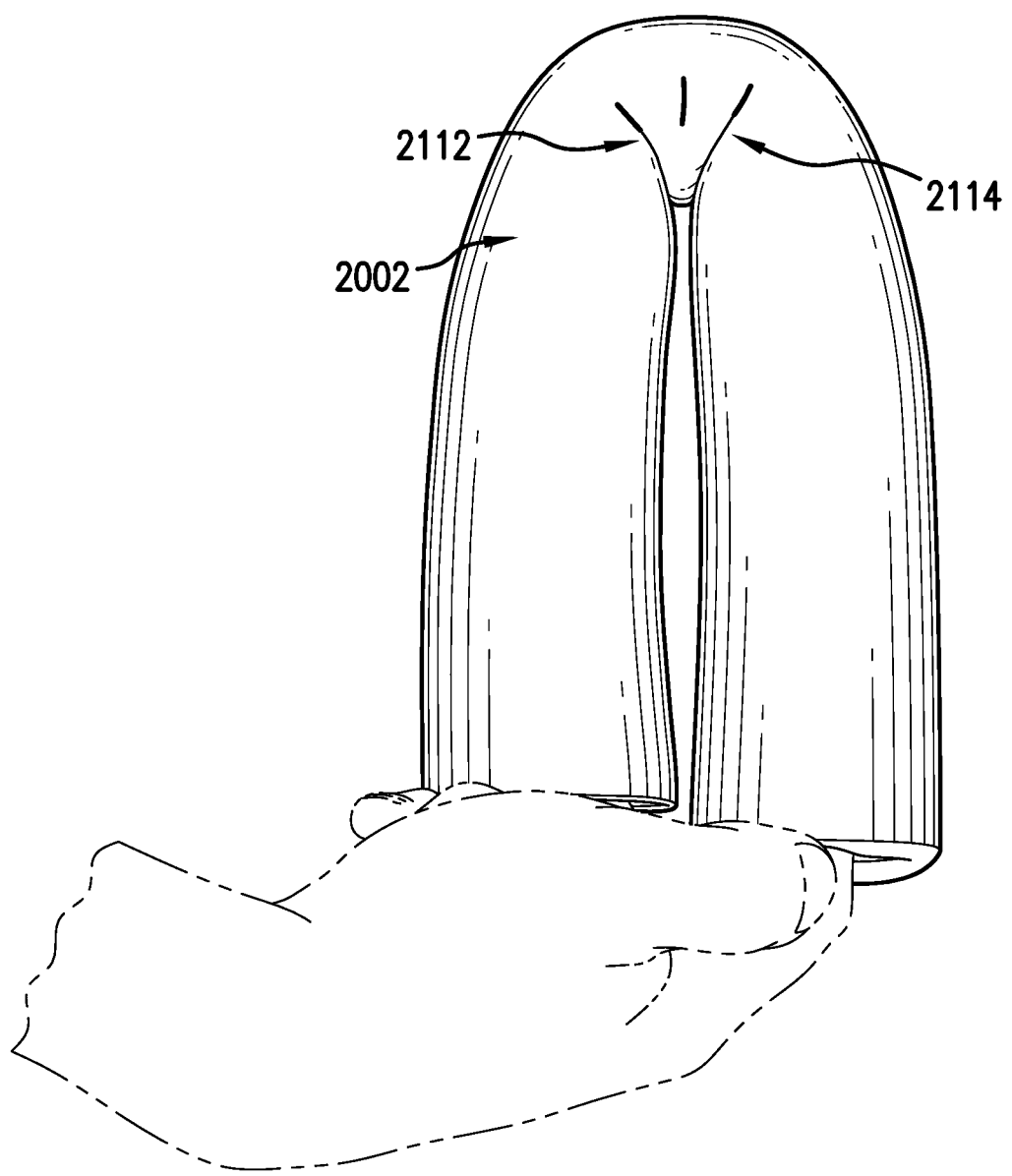
FIG. 21 is a drawing of the foam material tube of FIG. 20 with diamond-shaped hinge cuts (visible only from the side in FIG. 21) that may be used in a bumper for a garment device according to one embodiment of the present invention showing how the foam material tube may be bent/crimped to conform to the anatomy of the foot.
Figure 22:
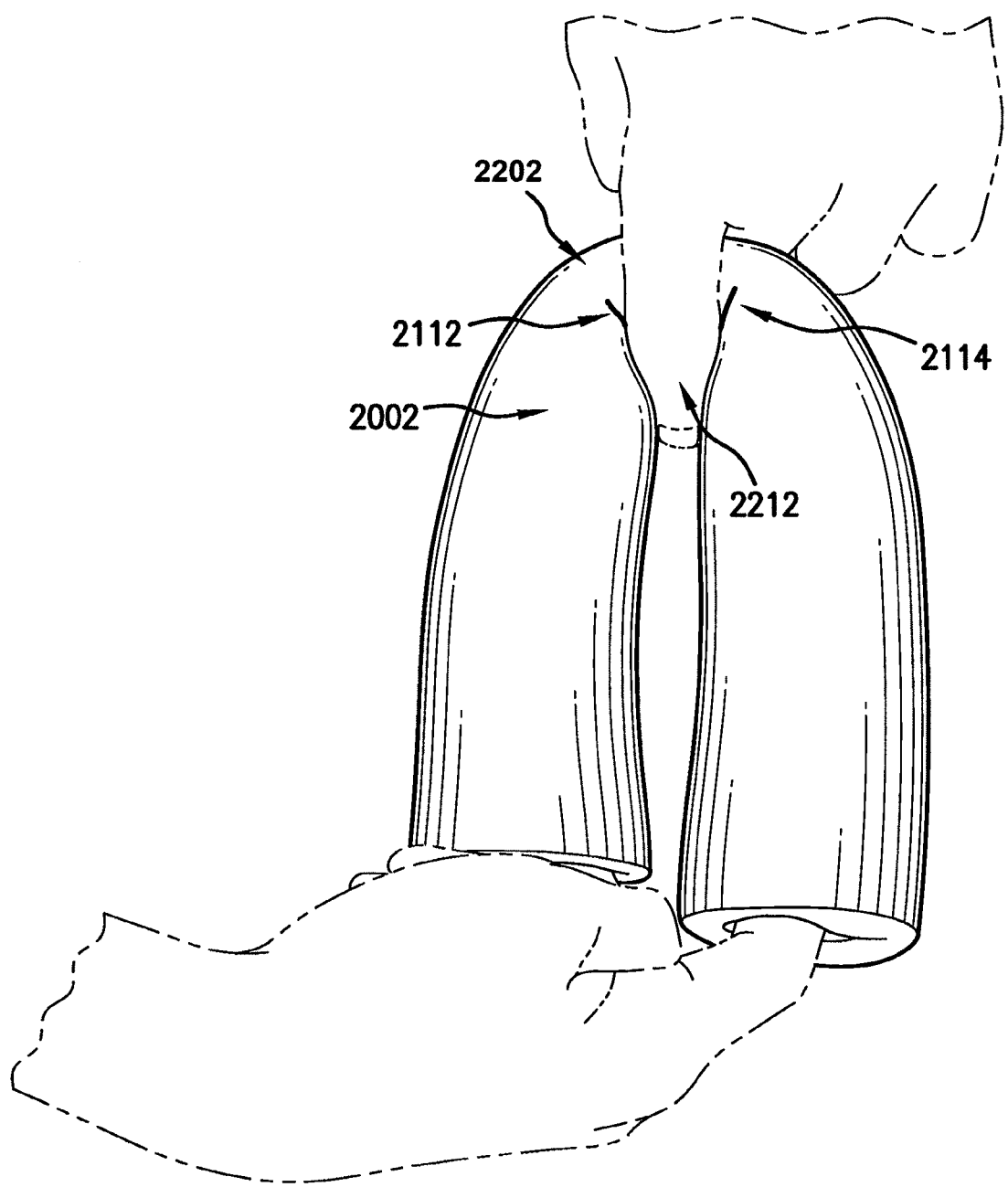
FIG. 22 is a drawing of the foam material tube of FIG. 21 showing how crimping of the tube captures a finger, similar to the way that the foam material tube would gently grip an Achilles tendon of an individual.

FIG. 20 shows a foam material tube 2002 that is being prepared to be used in a bumper (not shown) for a garment device of the present invention. Markings 2012 and 2014 show where diamond-shaped hinge cuts will be made to assist foam material tube 2002 in bending/crimping more readily. FIG. 21 shows foam material tube 2002 being bent/crimped, using diamond-shaped hinge cuts 2112 and 2114 that are visible only from the side in this figure. FIG. 22 shows how crimping at bend 2202 of foam material tube captures a finger 2212, similar to the way that foam material tube 2002 would capture an Achilles tendon of an individual.

Figure 23:
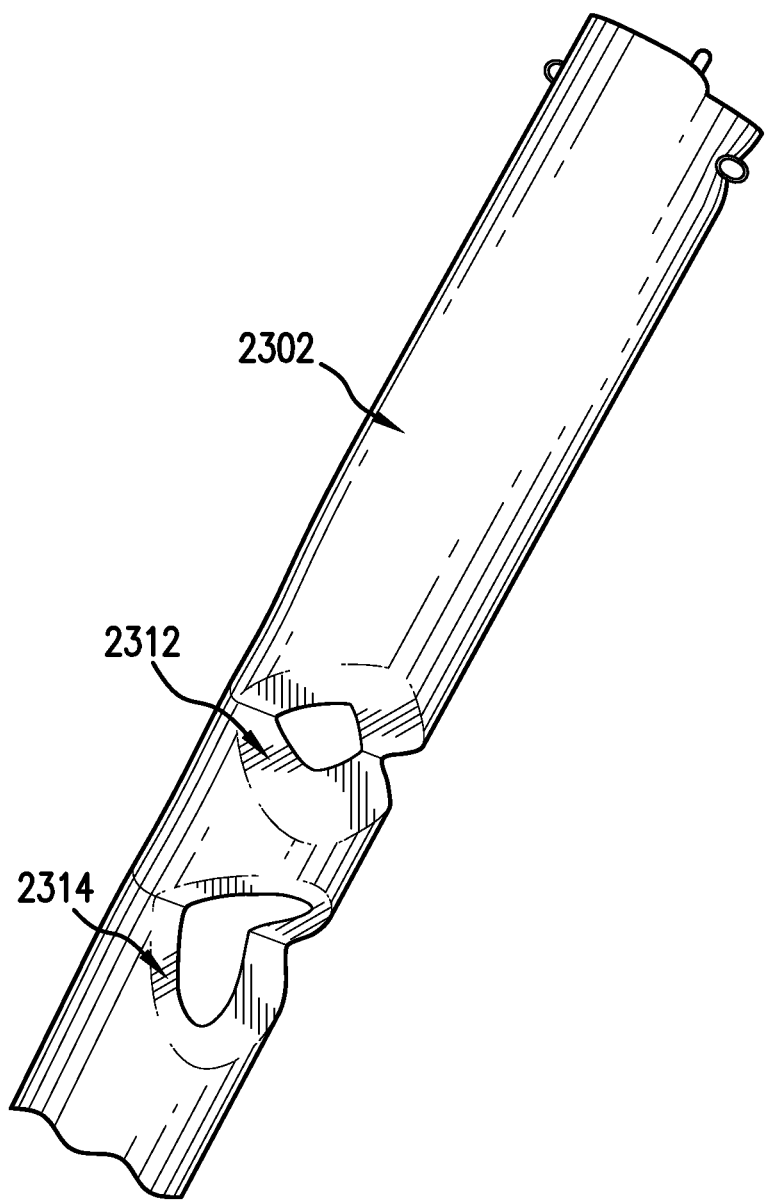
FIG. 23 is a drawing of a foam material tube according to one embodiment of the present invention showing diamond-shaped hinge cuts that assist the tube in bending/crimping more readily.
Figure 24:
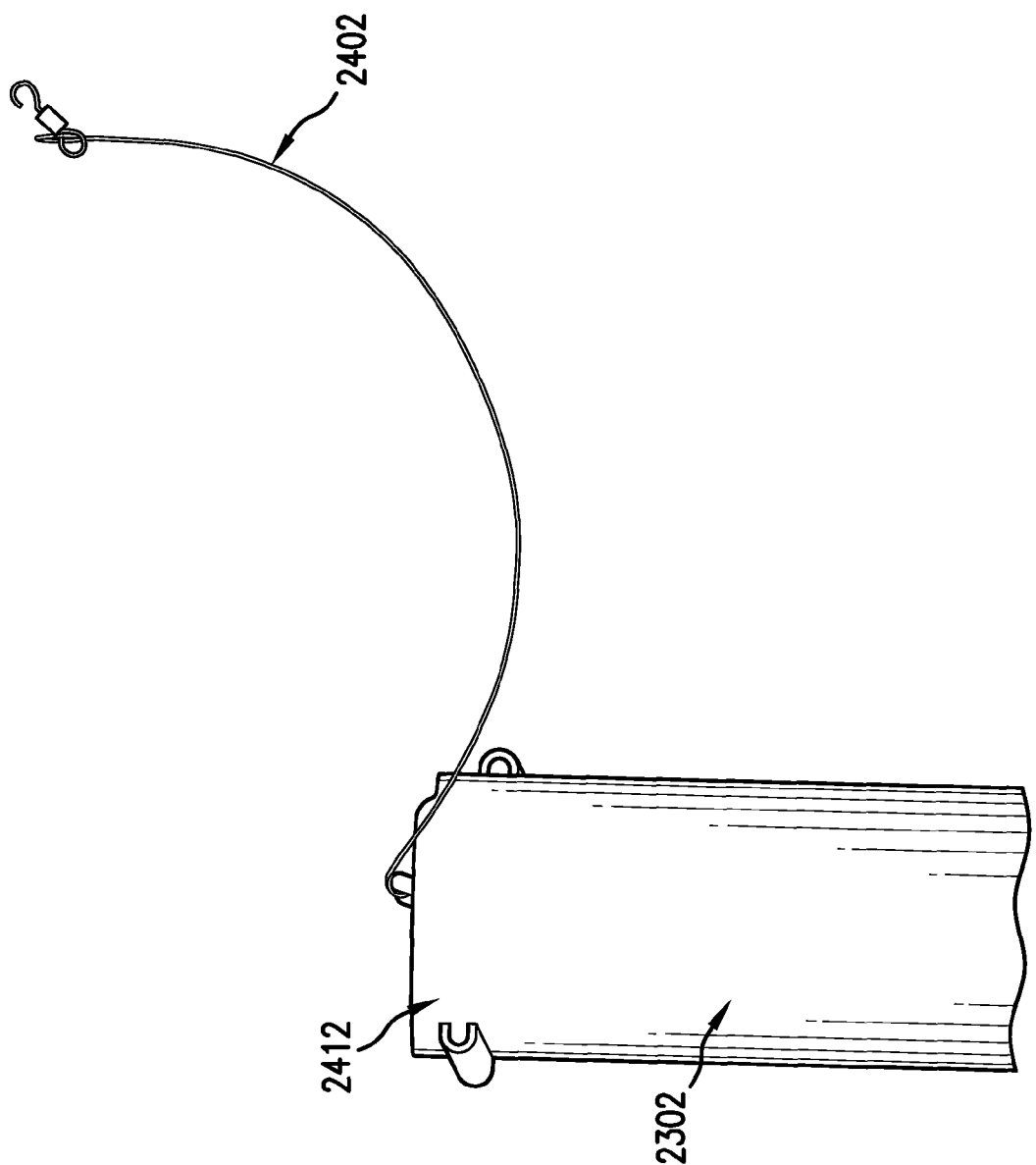
FIG. 24 is a drawing of the foam material tube of FIG. 23 showing a pull wire attached to one end of the foam material tube that assists the foam material tube in being more easily pulled into the sleeve of a bumper (not shown) of a foot garment device of the present invention.

FIG. 23 is a drawing of a foam material tube 2302 according to one embodiment of the present invention showing diamond-shaped hinge cuts 2312 and 2314 that assist foam material tube 2302 in bending/crimping more readily. FIG. 24 shows a pull wire 2402 attached to one end 2412 of foam material tube 2302 to allow foam material tube 2302 to be more easily pulled into and/or out of the sleeve of a bumper (not shown) of a foot garment device.

Although one type of pull wire is shown in FIG. 24, various types of devices such as loops, handles, strings, etc., may be used as a device that may be grasped by an individual to pull the foam material tube into the sleeve and/or out of the sleeve.

Figure 25:
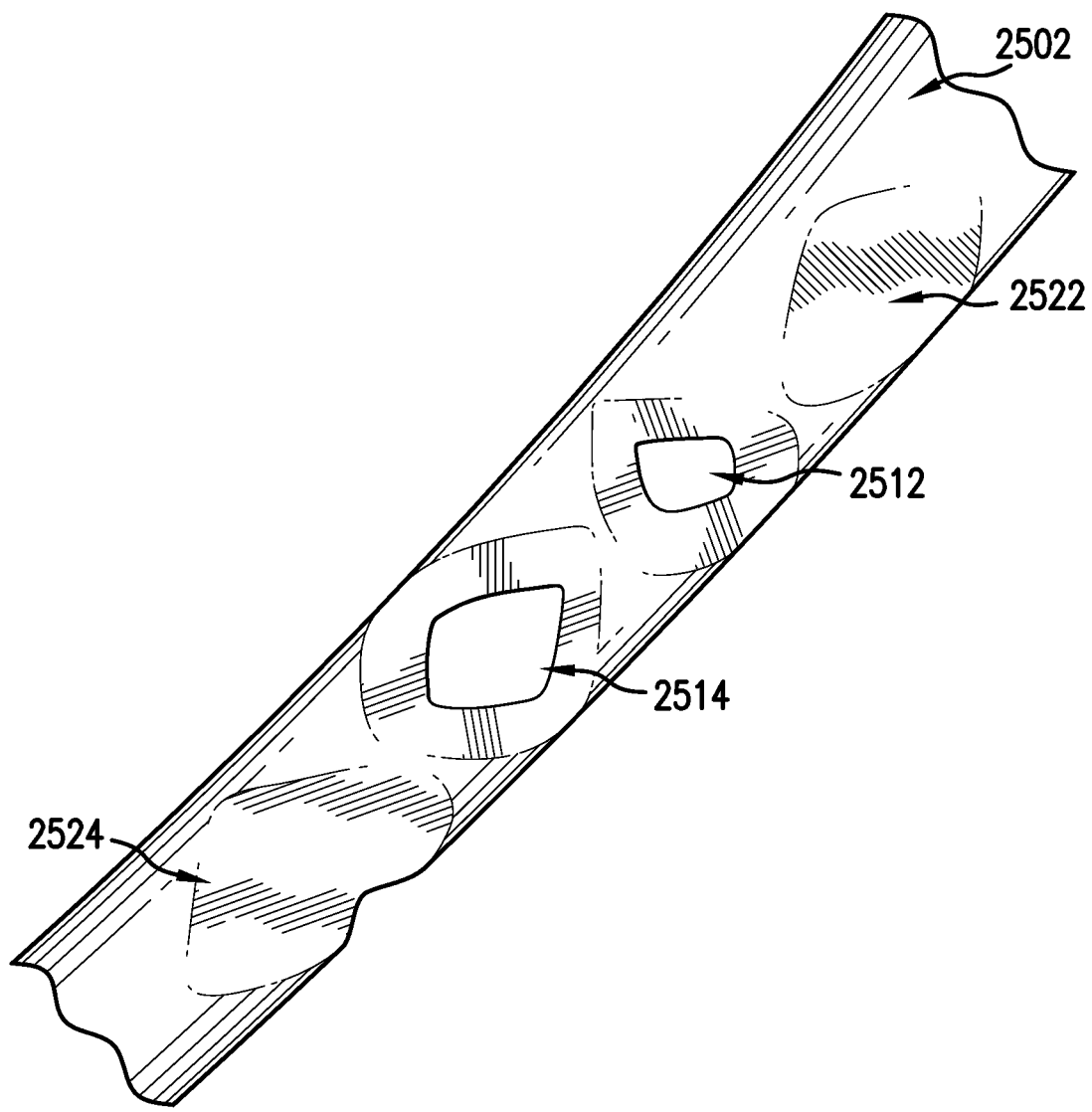
FIG. 25 is a drawing of a foam material tube according to one embodiment of the present invention showing diamond-shaped hinge cuts that assist the tube in bending more readily and additional anatomy cuts that have been made to accommodate the bony anatomy of an individual's foot.

FIG. 25 shows a foam material tube 2502, according to one embodiment of the present invention, showing diamond-shaped hinge cuts 2512 and 2514 that assist the tube in bending more readily. Additional anatomy cuts 2522 and 2524 have been made to accommodate the anatomy of an individual's foot (not shown in FIG. 25).

In preventing and treating a pressure ulcer, it is desirable to eliminate pressure over bony protrusions. Unlike the ski boot design, embodiments of the present invention may employ in a small slipper-like design that will not get in the way of doctors and nurses performing CPR or other emergency care, should it become necessary. Because of their bulk, large ski boot design devices get in the way and are not used, even when they should be, such as during long ambulance transport or during prolonged emergency room evaluation or surgical procedures.

The foot garment device of the present invention may be used in a variety of ways. For example, the foot garment device may be used on patients during prolonged bed rest such as on hospital general floors, in an intensive care unit (ICU), in a critical care unit (CCU), or when a patient is home/bed bound. The foot garment device of the present invention may also be used on patients who are sedated or unconscious and are lying on firm surfaces, such as during surgical procedures lasting more than two (2) hours, prolonged ambulance transportation, or prolonged diagnostic or treatment procedures. The foot garment device of the present invention may also be used on post-operative patients for bunion or other foot surgery.

Figure 26:
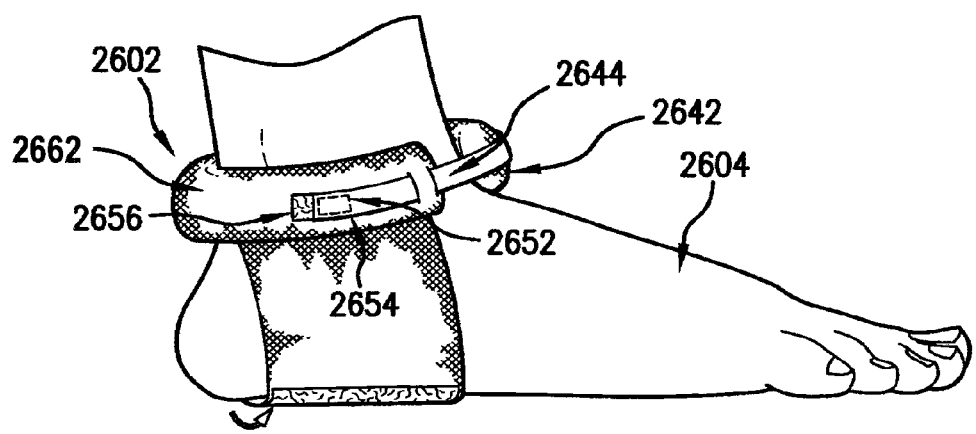
FIG. 26 is a drawing showing the side of a foot garment device secured to an individual's foot according to one embodiment of the present invention.
Figure 27:
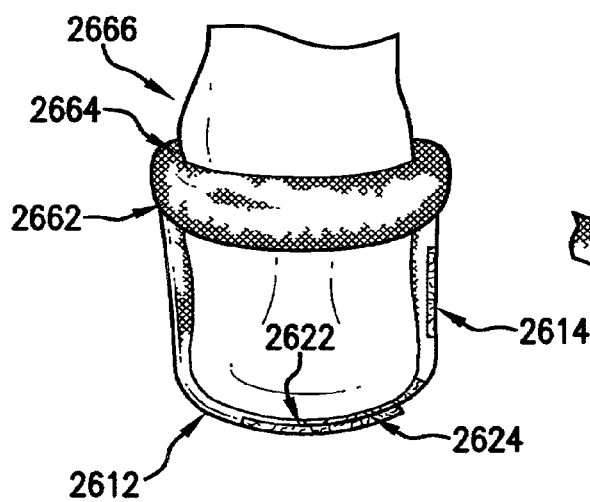
FIG. 27 is a drawing showing the back of the foot garment device of FIG. 26 secured to the individual's foot.

FIGS. 26 and 27 show a foot garment device 2602 secured to an individual's foot 2604, according to one embodiment of the present invention. Foot garment device 2602 includes a pair of adjustable lower flaps 2612 and 2614 having respective Velcro® strips 2622 and 2624 that releasably engage each other. Velcro® strips 2622 and 2624 are used to releasably engage lower flaps 2612 and 2614 to each other beneath foot 2604 and, thereby, form a sole. Foot garment device 2602 also includes a tendon cushion 2642, shown in detail in FIG. 28. An adjustable upper strap 2644 extends through loops 2646 and 2648 of tendon cushion 2642. Upper strap 2644 holds tendon cushion 2642 in place on the top of foot 2604 by Velcro Strips® 2652 (the location of one Velcro Strip® 2652 is shown by shadow lines) on each end 2654 of upper strap 2644 that releasably engage respective Velcro Strips® 2656 on each side of foot 2604 (only one side is shown in FIG. 26). Velcro Strips® 2656 are attached to a bumper 2662. Together, adjustable lower flaps 2612 and 2614 and upper strap 2644 are used to secure foot garment device 2602 to foot 2604. When foot garment device 2602 is secured to foot 2604, a bumper 2662 fits into a groove 2664 beneath ankle 2666 around the back of foot 2604.

Figure 28:
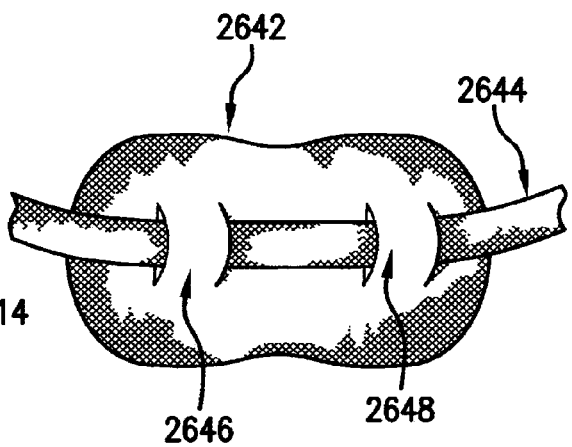
FIG. 28 shows a tendon cushion that is used with the foot garment device of FIGS. 26 and 27.

Although the tendon cushion loops are made by cuts in the tendon cushion of FIG. 28, in other embodiments of the present invention, these loops may be made in other ways, such as by using separate flaps that are sewn to or otherwise attached to the tendon cushion. The tendon cushion may be made of a soft material such as foam plastic polymer or other soft but resilient material.

A foot garment device 2902, according to one embodiment of the present invention, is shown in FIGS. 29 and 30. FIG. 29 shows a dorsal side 2904 of foot garment device 2902. FIG. 30 shows a plantar side 2906 of foot garment device 2902. Foot garment device 2902 includes a bumper 2912, adjustable upper flaps 2914 and 2916 and adjustable lower flaps 2918 and 2920. Bumper 2912 comprises a hollow sleeve 2922 in which is inserted foam material tube (not shown in FIGS. 29 and 30). Mounted on plantar side 2906 of bumper 2912 is a fleece cushioning pad 2924. Upper flaps 2914 and 2916 include respective Velcro® strips 2934 and 2936 that may be releasably engaged to each other to form an upper strap that wraps around the top of an individual's foot to which foot garment device 2902 is secured. As shown in FIGS. 29 and 30, Velcro® strip 2934 is a strip of loops and is located on plantar side 2906 of foot garment device 2902. Velcro® strip 2936 is a strip of hooks and is located on dorsal side 2906 of foot garment device 2902. Lower flaps 2918 and 2920 include respective Velcro® strips 2948 and 2950 that may be releasably engaged to each other to form a sole (not shown in FIGS. 29 and 30) that wraps around the sole of the foot of the individual. As shown in FIGS. 29 and 30, Velcro® strip 2948 is a strip of hooks on dorsal side 2904 and Velcro® strip 2950 is a strip of loops on plantar side 2906 of foot garment device 2902. End 2962 of sleeve 2922 is open to allow the foam material tube (not shown) to be inserted into sleeve 2922. End 2964 of sleeve 2922 is sewn closed. End 2962 may be closed by Velcro® strips 2968 and 2970, shown by dashed lines, on opposite sides of the interior of end 2962 of sleeve 2922. Lower flap 2918 and Velcro® strip 2948 are at an angle to provide for a more comfortable fit when lower flap 2918 and Velcro® strip 2948 are joined to lower flap 2920 and Velcro® strip 2950.

As shown in the embodiment of FIGS. 29 and 30, a Velcro® strip including hooks may be smaller than the Velcro® strip including loops. Also, although particular combinations of Velcro® strips of hooks and loops are shown in FIGS. 29 and 30, the flap and side including strips or loops may be different in different embodiments of the present invention. In one embodiment of the present invention, the strip of hooks on the upper flap may be about 1.5 inches in height by about 2 inches in width, and the mating strip of loops may be about 3.5 inches in height by about 2 inches in width. In one embodiment of the present invention, the Velcro® strips on the lower flaps may be 2 inches in height by 4 inches in width.

In one embodiment of the present invention, the fleece cushioning pad of FIGS. 29 and 30 may be about 2 inches in height by about 8 inches in width. In one embodiment, the bumper may be about 3.5 inches in height by about 21 inches in length. The upper flaps may be about 4 inches in width at their base, where they join the bumper, and about 3.5 inches in width at their tops and about 4 inches in height. The lower flaps may be about 6 inches in width at their base, wherein they join the bumper, and about 5 inches in width at their tops. The angled lower flap may have one side that is about 2.25 inches and one side that is about 3.375 inches. The other lower flap may have two sides that are about 2.25 inches in length. The distance between the upper flaps along the bumper may be about 11 inches and the distance between the lower flaps along the bumper may be about 8.25 inches. However, other embodiments of the present invention may have different dimensions.

Figure 31:
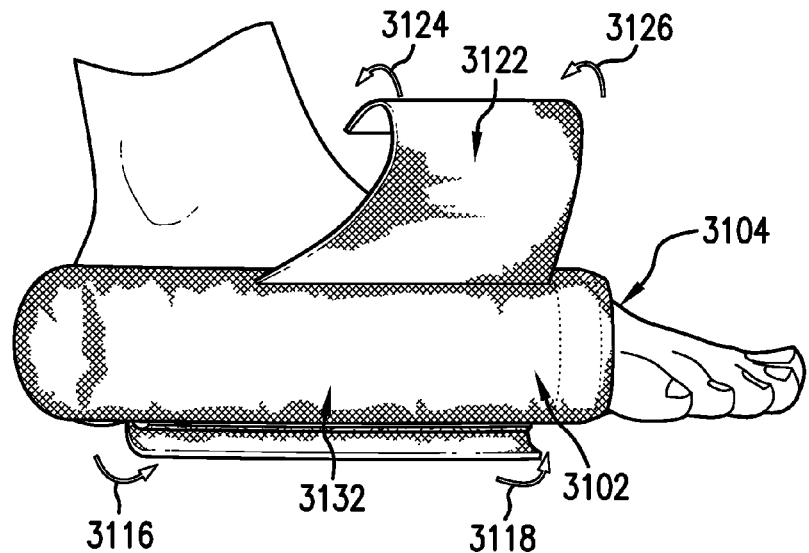
FIG. 31 is a drawing showing of a side of foot garment device secured to an individual's foot according to one embodiment of the present invention.
Figure 32:
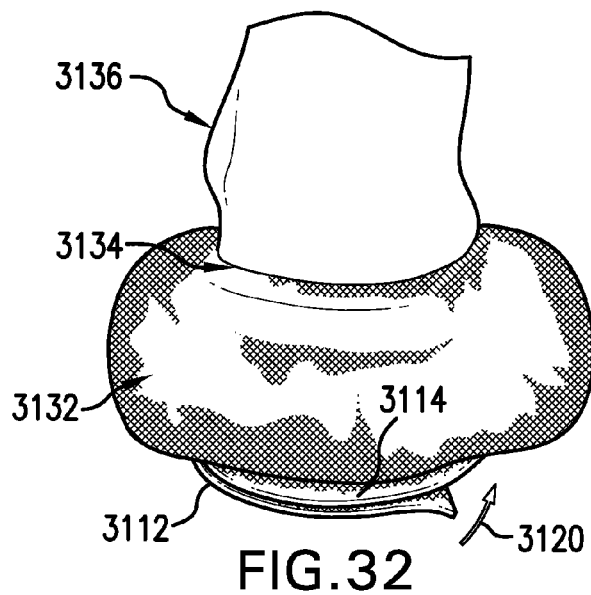
FIG. 32 is a drawing showing of the back of the foot garment device of FIG. 31 secured to an individual's foot.
Figure 33:
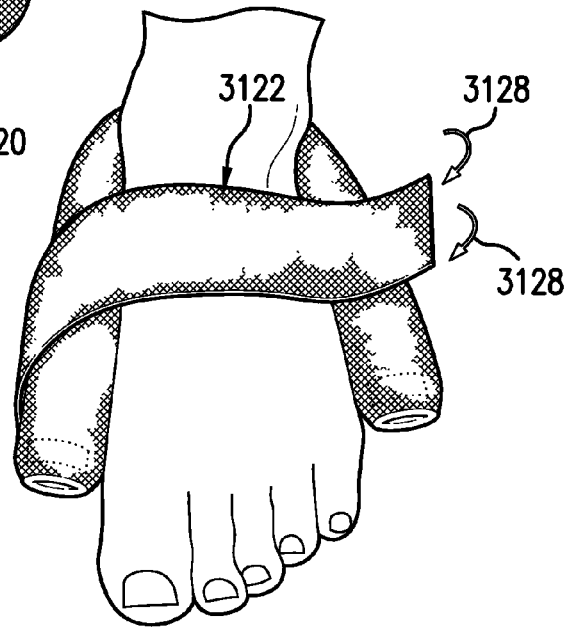
FIG. 33 is a drawing showing of the top of the foot garment device of FIG. 31 secured to an individual's foot.

FIGS. 31, 32 and 33 show a foot garment device 3102 secured to an individual's foot 3104 according to one embodiment of the present invention. Foot garment device 3102 includes a pair of adjustable lower flaps 3112 and 3114 having respective Velcro® strips (not shown). The Velcro® strips are used to releasably engage lower flaps 3112 and 3114 to each other beneath foot 3104, and, thereby, to form a sole, as shown by arrows 3116, 3118 and 3120. An adjustable upper flap 3122 includes a Velcro® strip (not shown) that may be releasably engaged to a Velcro® strip (not shown) on a bumper 3132 so that upper flap 3122 wraps around the top of foot 3104, as shown by arrows 3124, 3126, 3128 and 3130. Together, lower flaps 3112 and 3114 and upper flap 3122 are used to secure foot garment device 3102 to foot 3104. When foot garment device 3102 is secured to foot 3104, bumper 3132 fits into a groove 3134 beneath ankle 3136 around the back of foot 3104, extending from ankle 3136 to the base of foot 3104.

In one embodiment, the present invention provides a device comprising a foot garment including: a bumper for positioning around and below an ankle of an individual, and an upper strap and lower flap to form the sole of the slipper that are used to removably secure the foot garment to the foot of the individual, wherein the bumper comprises a sleeve with padding therein, and wherein the padding has a shape such that, when the foot garment is secured to the foot of the individual, the weight of the foot is distributed along the bumper so that bony excrescences of the foot do not contact the surface upon which the patient is lying and the weight of the foot is distributed along the padding.

In one embodiment, the padding may be a foam polymer tube that is either hollow or solid. The foam polymer tube may be removably inserted into the sleeve. The foam polymer tube may include a hinge that assists the foam polymer tube in wrapping around the back of the individual's foot underneath the ankle bones of the individual. The hinge may be formed by two diamond-shaped recesses in the foam polymer tube. The foam polymer tube may include recesses to prevent bony excrescences of the foot from contacting the foam polymer tube through the sleeve. The foam polymer tube may include an elongated member that may be grasped by an individual to pull the foam polymer tube into and out of the sleeve. In one embodiment of the present invention, the density of the foam polymer is chosen to provide sufficient support for the ankle over an extended period of time.

In addition to plastic polymer foam, other soft, resilient materials may be used as a tubular or cylindrical insert with the sleeve of the present invention. For additional cushioning, the Achilles side of the sleeve may include a pad of cushioning material, such as a fleece cushioning pad.

In one embodiment of the present invention, the sleeve is open at both ends. In one embodiment of the present invention, the sleeve may be sealed at one end. In one embodiment of the present invention, on one or both ends of the sleeve a releasable fastening device may be used to releasably close the end of the sleeve. In one embodiment, the releasable fastening device may be two strips of Velcro® on opposite sides of the interior of the sleeve that releasably engage each other.

Although in the embodiments shown and described above, the hollow sleeve has one open reclosable end and one closed end, in other embodiments of the present invention, both ends of the hollow sleeve may be reclosable. In still other embodiments, both ends may be sewn closed after the padding is inserted in the hollow sleeve.

In one embodiment of the present, the lower adjustable flap(s) may include a reinforcement to provide a firm sole support. Such a reinforcement may take the form of a plastic insert inserted in the flap(s), sewn into the flaps, etc.

In one embodiment of the present invention, there is provided a method for preventing or helping to prevent or heal pressure ulcers of the foot employing a foot garment of the present invention.

All documents, patents, journal articles and other materials cited in the present application are incorporated herein by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A device comprising: a foot garment comprising:
  a bumper including a bend portion configured to wrap around and below an ankle of an individual, the bumper having a height defined by a distance between a dorsal and plantar side thereof, the height of the bumper configured such that the bumper can be positioned between the ankle and a sole of a foot of the individual,
  one or more upper adjustable flaps extending from the dorsal side of the bumper and configured to wrap around a top of the foot of the individual, and
  one or more lower adjustable flaps extending from the plantar side of the bumper and configured to wrap around the sole of the foot of the individual to define a device sole,
  wherein the bumper comprises a hollow sleeve for receiving padding therein.

2. The device of claim 1, wherein a first end of the bumper includes an opening configured to receive the padding therethrough, the opening located between the dorsal and plantar sides.

3. The device of claim 2, wherein the padding is removable padding.

4. The device of claim 3, wherein the removable padding comprises a pull-through-assist device that extends from the removable padding and that may be pulled on to pull the removable padding into and/or out of the hollow sleeve.

5. The device of claim 2, wherein the padding has a shape such that, in response to the foot garment being secured to the foot of the individual, the weight of the foot is distributed along the bumper.

6. The device of claim 3, wherein when the foot of the individual is lying on a horizontal surface, bony excrescences of the foot are prevented from contacting the horizontal surface by the bumper.

7. The device of claim 2, wherein the padding comprises a foam material tube comprising two or more hinge cuts for assisting the foam material tube in bending around the ankle of the individual.

8. The device of claim 7, wherein the padding comprises one or more anatomy cuts for accommodating bony anatomy of the foot of the individual.

9. The device of claim 2, wherein the padding comprises an elongated member comprising memory foam and wherein the elongated member comprises two or more hinge grooves for assisting the elongated member to bend around the ankle of the individual.

10. The device of claim 1, wherein the one or more lower adjustable lower flaps comprise a first adjustable lower flap comprising a first strip of a hook-and-loop fastening device and a second adjustable lower flap comprising a second strip of the hook-and-loop fastening device for releasably engaging the first strip of the hook-and-loop fastening device.

11. The device of claim 10, wherein the first strip is a strip of hooks, and wherein the hooks are oriented away from the foot of the individual in the device sole.

12. The device of claim 1, wherein the one or more adjustable upper flaps comprise a first adjustable upper flap comprising a first strip of a hook-and-loop fastening device and a second adjustable upper flap comprising a second strip of the hook-and-loop fastening device for releasably engaging the first strip of the hook-and-loop fastening device.

13. The device of claim 11, wherein the first strip is a strip of hooks and wherein the hooks are oriented away from the top of the foot of the individual when the first and second adjustable flaps are wrapped around the top of the foot of the individual.

14. The device of claim 1, wherein the one or more adjustable upper flaps comprise a single upper flap that comprises a first strip of a hook-and-loop fastening device for releasably engaging a second strip of a hook-and-loop fastening device on the hollow sleeve.

15. The device of claim 14, wherein the second strip is a strip of hooks.

16. The device of claim 1, wherein the hollow sleeve comprises at least one reclosable end.

17. A method comprising: (a) providing a foot garment comprising: a bumper including a bend portion configured to wrap around and below an ankle of an individual, the bumper having a height defined by a distance between a dorsal and plantar side thereof, the height of the bumper configured such that the bumper can be positioned between the ankle and a sole of a foot of the individual and one or more upper adjustable flaps and one or more lower adjustable flaps for securing the foot garment to a foot of the individual, and (b) securing the foot garment to the foot of the individual, wherein the bumper comprises a hollow sleeve and padding therein, wherein the one or more lower adjustable flaps comprise a device sole when the foot garment is secured to the foot of the individual, and wherein the one or more upper adjustable flaps wrap around a top of the foot of the individual when the foot garment is secured to the foot of the individual.

18. The method of claim 17, further comprising the following step: (c) inserting the padding in the hollow sleeve prior to step (b).

19. The method of claim 18, wherein the padding comprises a foam material tube comprising two or more hinge cuts for assisting the foam material tube in bending around the ankle of the individual.

20. The method of claim 19, further comprising the following step: (d) cutting one or more anatomy cuts in the foam material tube for accommodating bony anatomy of the foot of the individual.

\* \* \* \* \*